United States Patent
Kawaguchi et al.

(10) Patent No.: US 7,460,894 B2
(45) Date of Patent: Dec. 2, 2008

(54) BIOLOGICAL OPTICAL MEASURING INSTRUMENT

(75) Inventors: Tsuneaki Kawaguchi, Shounan-machi (JP); Eiji Furuzono, Ushiku (JP); Mikihiro Kaga, Abiko (JP); Satoshi Onozuka, Ryugasaki (JP)

(73) Assignee: Hitachi Medical Corporation, Tokyo (JP)

( * ) Notice: Subject to any disclaimer, the term of this patent is extended or adjusted under 35 U.S.C. 154(b) by 905 days.

(21) Appl. No.: 10/484,004

(22) PCT Filed: Jul. 19, 2002

(86) PCT No.: PCT/JP02/07350

§ 371 (c)(1),
(2), (4) Date: Jun. 22, 2004

(87) PCT Pub. No.: WO03/008944

PCT Pub. Date: Jan. 30, 2003

(65) Prior Publication Data

US 2004/0236195 A1    Nov. 25, 2004

(30) Foreign Application Priority Data

Jul. 19, 2001 (JP) ............... 2001-220093
Mar. 27, 2002 (JP) ............... 2002-090000

(51) Int. Cl.
*A61B 5/1455* (2006.01)

(52) U.S. Cl. ............... 600/310; 600/473; 600/476

(58) Field of Classification Search ............... 600/309, 600/310, 473, 476
See application file for complete search history.

(56) References Cited

U.S. PATENT DOCUMENTS

| 4,796,236 A | * | 1/1989 | Welles et al. | 367/7 |
| 5,632,272 A | * | 5/1997 | Diab et al. | 600/323 |
| 5,919,134 A | * | 7/1999 | Diab | 600/323 |
| 5,995,858 A | * | 11/1999 | Kinast | 600/323 |
| 6,011,401 A | | 1/2000 | Henry et al. | |
| 2002/0098120 A1 | * | 7/2002 | Blazewicz et al. | 422/82.07 |

FOREIGN PATENT DOCUMENTS

| JP | 58 150624 | 8/1983 |
| JP | 2 257929 | 10/1990 |
| JP | 4 030404 | 2/1992 |
| JP | 6 034681 | 2/1994 |
| JP | 8 278250 | 10/1996 |
| JP | 8 512217 T | 12/1996 |
| JP | 2000 300569 | 10/2000 |
| JP | 2000 304695 | 11/2000 |
| JP | 2001 159601 | 6/2001 |
| WO | WO 99/40841 | 8/1999 |

OTHER PUBLICATIONS

Wakutsu, T.; Serizawa, M; "An OFDM Carrier Frequency Offset Estimation Scheme Utilizing Power Differences of Pilot Sub-Carriers," The Institute of Electronics, Information and Communication Engineers, RCS 99-82 (1999-8), pp. 35-40. In Japanese.

* cited by examiner

*Primary Examiner*—Eric F Winakur
*Assistant Examiner*—Etsub D Berhanu
(74) *Attorney, Agent, or Firm*—Antonelli, Terry, Stout & Kraus, LLP.

(57) ABSTRACT

A biomedical optical measurement apparatus comprising a light source unit for generating an inspection light containing multiple lights modulated at different frequencies, a light-receiving unit for receiving the light generated at said light source unit and passing through an object to be examined and for outputting the electric signals with the intensity corresponding to the received inspection light, and a detection means for detecting a signal with the same frequency of the reference signal in the output from said light-receiving unit. The detection means comprises an analog-digital conversion means for outputting digitized data by converting an input signal to a digital signal, a storage means for storing digitized data of multiple reference signals, a digital multiplication means for multiplying digitized data of input signals outputted from the analog-digital converting means by the digitized data of the reference signals read out from the storage means and for outputting the product of multiplication, and a digital band-limitation means for taking out DC data from the output from the digital multiplication means. Reference signal generating circuits of a number equal to that of frequencies of detected signals, which has been necessary for the conventional instrument, can be replaced by a single memory means and the configuration of the instrument can be simplified. Changes in frequency can be easily coped with by only re-writing the data of the storing means.

14 Claims, 16 Drawing Sheets

US 7,460,894 B2

BIOLOGICAL OPTICAL MEASURING INSTRUMENT

CROSS REFERENCE TO RELATED APPLICATION

This Application is a U.S. National Stage Application filed under 35 U.S.C. § 371 of PCT/JP02/07350 Jul. 19, 2000.

FIELD OF INVENTION

The present invention relates to a biomedical optical measurement apparatus, which measures inside the living body by receiving a light that has passed through the living body. Particularly, the invention relates to the biomedical optical measurement apparatus equipped with an improved detection circuit, which can distinguish and detect a light to be detected at multiple light-receiving positions.

Prior Art

The field of clinical medicine and brain science are strongly expecting to have a measuring instrument, which allows easy measurement inside the living body without giving hazardous damage to a living body. To meet such expectation, biomedical optical measurement apparatuses for measuring inside the living body by receiving a light passing through the living body, such as those disclosed and claimed in the Japanese Patent Application Laid-Open Nos. 9-149903 and 2000-300569 have been proposed. These biomedical optical measurement apparatuses described in such patent publications have a configuration in which an inspection light composed of multiple lights modulated at different frequencies is irradiated onto the multiple positions of an object to be examined, only the light passing through the object is received and signals with specific frequencies are detected from electric signals with the intensity corresponding to the passed light using a lock-in amplifier (biomedical) to obtain information on the living body, particularly on the blood circulation, in the area including multiple irradiation positions.

There is also a biomedical optical measurement apparatus, which is equipped with a time-sharing light irradiating and receiving means in order to obtain information from multiple irradiation positions. This biomedical optical measurement apparatus does not use an aforementioned lock-in amplifier but has a configuration wherein the light is irradiated sequentially from the light source unit (light emitting probe) and received sequentially at the light-receiving unit (light-receiving probe) with both irradiation and receiving of light being controlled by clock signals, thereby identifying measurement position.

Configuration and problems of the detection circuit used in these conventional biomedical optical measurement apparatuses are explained below.

FIG. 14 shows a block diagram showing a schematic configuration of a lock-in amplifier employed in the conventional biomedical optical measurement apparatuses. The light-receiving element 171 receives an inspection light that passed through an object to be examined, performs photoelectric conversion and outputs electric signals with the intensity corresponding to the light to the amplifier 172. The signal amplified by the amplifier 172 is inputted as an input signal 173 in each lock-in amplifier. The input signal 173 is a synthesized signal made of multiple signals with different frequencies. Reference signal generating circuits 1751 to 175n output reference signals having the same frequencies as those of signals to be detected in the multipliers 1741 to 174n, respectively. The multipliers 1741-174n multiply individual input signal 173 by the reference signal from the reference signal generating circuits 1751 to 175n and output the products in the low-pass filters 1761 to 176n. The low-pass filters 1761 to 176n take out the direct current component from the output at multipliers 1741 to 174n and output them as output signals 1771 to 177n. The multipliers 1741 to 174n, the reference signal generating circuits 1751 to 175n and the low-pass filters 1761 to 176n are provided in the number of frequencies to be detected (n). The outputs from the low-pass filters 1761 to 176n are introduced through the A/D converter, which is not shown in the figure, into the processing circuit of PC and undergo signal processing.

FIG. 15 shows a block diagram showing a detailed configuration of one of the multiple lock-in amplifiers shown in FIG. 14. Since each lock-in amplifier has the same configuration, except frequency of a reference signal to be used, the lock-in amplifier shown at the top of FIG. 14 is explained. This lock-in amplifier is configured to detect a direct current component of the input signal having the same frequency as that of reference signal by amplifying the output from the amplifier 172, which inputs signals from the light-receiving element 171, by dividing it into two amplifiers 183 and 184, in which positive/negative switching is performed, and then by outputting the outputs from said amplifiers 183 and 184 after switching at the switching circuit 185, which switches polarity according to the frequency of the reference signals. Specifically, the signal amplified by the amplifier 172 (a synthesized signal made of multiple signals with different frequencies) is outputted as divided into the amplifier 183 and 184. The amplifier 183 amplifies the input signal as it is, that is, after multiplying by +1, and output it at the first terminal of the switch circuit 185. The amplifier 184 reverses the polarity of input signal, or multiple by −1, and output it at the second terminal of the amplifier 184. The switch circuit 185 supplies output from the amplifier 183 or 184 to amplifier 186 by alternately switching between first and second terminal in accordance with the reference signal F1 outputted from the reference signal generating circuit 1751. Here, the reference signal F1 is a signal whose frequency is the same as that of the signal to be detected at this lock-in amplifier 185. The amplifier 186 amplifies the signal outputted from the switch circuit 185 and outputs it to the low-pass filter 1761.

FIG. 16 shows a timing chart of signal waveforms, which describes the action of the lock-in amplifier shown in FIG. 15. FIG. 16(A) shows a case in which the signals to be detected are locked-in by the lock-in amplifier, while FIG. 16(B) shows the case in which other signals than those to be detected are not locked in. The signal to be detected is a signal whose frequency is same as that of the reference signal Fn in FIG. 16(A). The input signals contain the signal whose frequency is same as that of reference signal Fn. When the signal AMP1 (I) outputted from the amplifier 172 has the same frequency as the reference signal Fn, the signal AMP1 (P) outputted from the amplifier 183 is the same with the signal AMP1 (I), while the signal AMP1 (N) outputted from the amplifier 184 is an inverted signal of AMP1 (I). When these signals AMP1 (P) and AMP1 (N) are outputted from the amplifiers 183 and 184, the switch circuit 185 is switched by the reference signal Fn, thereby outputting a signal AMP1 (O) from the amplifier 186. The direct current component of this signal AMP1 (O) passes through the low-pass filter 176 (1761-176n) and is outputted as a detection signal LPF1.

As shown in FIG. 16(B), if the signal AMP2 (I) outputted from the amplifier 172 has a different frequency from that of the reference signal Fn, a signal AMP2 (O) is outputted from the amplifier 186. Although a direct current component of this signal AMP2 (O) passes through the low-pass filter 176 and is outputted as a detection signal LPF2, the direct current component is zero because its frequency is different from that of reference signal Fn. The lock-in amplifier will, thus, detect only a signal with a particular frequency.

As mentioned above, the lock-in amplifiers used in the conventional biomedical optical measurement apparatuses required multipliers, reference signal generating circuits and low-pass filters in the numbers equal to the number of frequencies of signals to be detected. If the frequency of the signal to be detected is changed, therefore, a different reference signal generating circuit had to be provided.

Moreover, if the signal to be detected has a phase difference from the reference signal Fn and/or if the phase difference varies in the lock-in amplifier of the biomedical optical measurement apparatus as shown in FIG. 15, there occurs a problem that the detection signal to be outputted from the low-pass filter 176 attenuates more than usual and leads to a deteriorated S/N ratio.

FIG. 17 shows a timing chart of signal waveforms, which explains the action of the lock-in amplifier shown in FIG. 15 when the signal to be detected has a phase difference from that of the reference signal and the phase difference varies. FIG. 17(A) shows the case, in which the signal to be detected have a phase difference from the reference signal, while FIG. 17(B) shows the case, in which the phase difference of the signal to be detected varies for the reference signal.

As shown in FIG. 17(A), if the phase of signal AMP3 (P) outputted from the amplifier 183 is delayed from that of reference signal Fn, such a signal as AMP3 (O) is output from the amplifier 186, and thereby a low level detection signal LPF3 with a small S/N ratio is output from the low-pass filter 176. Similarly, as shown in FIG. 17(B), when the phase of the signal AMP4(O) outputted from the amplifier 183 changes diversely for the reference signal Fn, the amplifier 186 may output a signal such as AMP4(O). It is not favorable because the low-pass filter 176 outputs a detection signal LPF4, whose level changes in accordance with the phase changes and whose S/N ratio is unstable.

FIG. 18(A) shows a schematic configuration of a biomedical optical measurement apparatus equipped with a time-sharing irradiating- and light-receiving means. This biomedical optical measurement apparatus is configured, as the biomedical optical measurement apparatus in FIG. 14, to receive an inspection light passing through an object to be examined at a light-receiving element 161, to convert the light to an electrical signal (photoelectric conversion), output the signal corresponding to the intensity of light into the amplifier 162 and input the signals amplified by the amplifier 16 into the A/D converter 163.

However, this biomedical optical measurement apparatus is equipped with a clock (timing signal) for sequentially processing signals to be outputted from the light-receiving element in a time-sharing manner. This clock is outputted from the control unit, which is not illustrated, and controls the timing of irradiating a light from the light source unit as well as the sampling timing in the A/D converter 163. That is, the A/D converter 163 performs analog-digital conversion at a time synchronized with the clock signal CLOCK and outputs them in the arithmetic operation unit (PC) 169.

FIG. 18(B) shows a timing chart of an exemplary action. In FIG. 18(B), signals S1 to S5, whose irradiation timing from each light source is shown, are outputted in a desired time-sharing timing by each light source. These signals S1 to S5 are outputted as a synthesized signal D from the amplifier 162 into the A/D converter 163. The A/D converter 163 converts the signal from analog to digital signal with the timing of clock signal CLOCK and outputs the digital signal as a detection signal.

In biomedical optical measurement apparatuses, signals detected in the light-receiving unit are ones passed through an object to be examined among incident lights from the light source unit, and the level of light intensity is extremely low. FIG. 19 shows a biomedical optical measurement apparatus, which is modified by improving the biomedical optical measurement apparatus FIG. 18(A) so as to increase an S/N ratio of the signal detected in the light-receiving unit. The biomedical optical measurement apparatus shown in FIG. 19 is equipped with an integrator 170 prior to the AD converter 163. The integrator 170 is reset at a time synchronized with the clock signal CLOCK, while the A/D converter 163 performs A/D conversion at a time synchronized with the clock signal CLOCK. By installing this integrator 170, the level of the detection signal IntD at the time of analog-digital conversion by the A/D converter becomes higher than that of the signal D as shown in FIG. 19(B), thereby leading to the sufficiently large S/N ratio.

In the biomedical optical measurement apparatus equipped with such time-sharing light-irradiating and receiving means, if the level required for the detection signal IntD is about the level of the signal D, sampling frequency can be accelerated by making the time interval of signals S1 to Sn closer as shown in FIG. 20(B). However, if there is a phase change as the signal D shown in FIG. 20(B), the acceleration may lead to the condition in which the integrator will not be sufficiently reset at a certain reset time, and the level of remaining preceding signals may affect the subsequent detection signal IntD. This makes accurate measurement of the intensity of multiple signals at the multiple irradiating positions difficult, thereby reducing the reliability of measurement results.

As described above, the function required for the detection unit of the biomedical optical measurement apparatus is to distinguish and detect a transmitted light that corresponds to the light irradiated onto multiple positions from the light source unit. However, the conventional biomedical optical measurement apparatus equipped with a conventional lock-in amplifier using reference signals of multiple frequencies has various unfavorable problems. They include that the instrument should be large enough to accommodate multiple reference signal generating circuits and is not able to cope with changes in the frequency of the reference signal. Also there is a problem common to instruments of a time-sharing light-irradiating and receiving system that a phase change of the detection signal deteriorates S/N ratio and causes insufficient distinction.

The first object of this invention, therefore, is to provide a biomedical optical measurement apparatus wherein a lock-in amplifier comprises a fewer element units. The second object is to provide a biomedical optical measurement apparatus, which is easily able to cope with changes in the frequency. This invention has the third object to provide a biomedical optical measurement apparatus, which can detect the signals without deteriorating S/N ratio even when there is a phase difference between reference signals and signals to be detected. This invention also has an object to provide an biomedical optical measurement apparatus equipped with a time-sharing light irradiating and receiving means, which properly distinguishes signals to be detected continuously in a time-sharing manner even if there is phase fluctuation in the signals to be detected, and which has an improved reliability in measurement. Further, this invention has an object to provide a detection circuit, which can be applied to all types of biomedical optical measurement apparatuses.

DISCLOSURE OF THE INVENTION

The biomedical optical measurement apparatus of this invention comprises a light source means for generating an inspection light containing multiple lights modulated at different frequencies, a light-receiving means for receiving the light generated at the aforementioned light source means and passing through an object to be examined and for outputting electric signals with the intensity corresponding to the received inspection light, and a detection means for detecting a signal with the same frequency of the reference signal from the output from said light-receiving means, wherein said detection means comprises an analog-digital conversion means for outputting digitized data by converting an input signal to a digital signal, a storage means for storing digitized data of multiple reference signals, a digital multiplication means for multiplying digitized data of input signals outputted from said analog-digital converting means by the digitized data of the reference signals read out from said storage means and for outputting the product of multiplication, and a digital band-limitation means for taking out DC data from the output from said digital multiplication means (Claim 1).

According to this biomedical optical measurement apparatus, by storing digitized data of multiple signals in the storage means, it becomes unnecessary to provide reference signal generating circuits in a number equal to the number of frequencies of the signal to be detected. Also, it can easily cope with changes in the frequency of the signal to be detected by rewriting data in the storage means and storing digitized data of reference signals with new frequencies.

In the aforementioned biomedical optical measurement apparatus of this invention, said digital multiplication means and said digital band-limitation means are composed by a digital signal processor (Claim 2). Use of the digital signal processor can significantly reduce the scale of the circuit.

The biomedical optical measurement apparatus of this invention further comprises a delaying means for delaying digitized data of the reference signals (Claim 3). The delaying means is to correct a phase difference, if any, between the signal to be detected and the reference signal. Correction of the phase difference can prevent a decline of the level of the signal to be detected and ensure a sufficiently high S/N ratio.

The biomedical optical measurement apparatus of this invention further comprises a function generating means which inputs the digitized data of said reference signal and generates a function that becomes "0" or "close to 0" near the level changing point of the digitized data (Claim 4).

Phase difference between the signal to be detected and the reference signals is generated and changes near the area where the reference signal level changes from "0" to "1" or from "1" to "0", namely near the level changing point. Therefore, by generating a specific function in accordance with the reference signal, namely, the function which becomes "0" or "close to 0" near the level changing point of reference signal (for example, trigonometric function, Gaussian function or Window functions, such as Hamming and Hanning window functions), multiplying the signal to be detected by said function and applying filtering processing to them, the level of detection signals will not change and becomes relatively stable even if the phase changes.

Further, the biomedical optical measurement apparatus of this invention comprises a light source means for generating multiple inspection lights in a time-sharing manner, a light-receiving means for sequentially receiving the inspection light which is generated at said light source means and passing through an object to be examined, and a detection means for detecting signals from said light-receiving means and for outputting them as signals for each of the multiple inspection lights; wherein said detection means further comprises an analog-digital conversion means for converting analog input signals to digital signals and for outputting digitized data of the input signals, a clock means for generating a timing signal so that said analog-digital converting means can begin analog-digital conversion at a specified sampling timing, a function generating means for generating functions which become "0" or "close to 0" near the sampling time of said input signals, a digital multiplying means for multiplying digitized data of input signals outputted from said analog-digital converting means by the function of said function generating means and for outputting the product of multiplication (Claim 8).

In detecting multiple inspection lights to be outputted in a time-sharing manner by the time-sharing light irradiating and receiving function, this biomedical optical measurement apparatus can detect individual inspection lights accurately without overlapping of preceding signals over detected signals.

Further, the biomedical optical measurement apparatus of this invention, which has a aforementioned time-sharing light-irradiating and receiving function, comprises an integrating means for adding the output from said digital multiplication means posterior the digital multiplication means (Claim 9). By equipping the integrating means, the S/N ratio of the signals can be improved.

Further, the biomedical optical measurement apparatus of this invention is equipped with, as a detection means, a digital lock-in amplifier comprising aforementioned analog-digital conversion mean, digital multiplication means and digital band-limiting means, and a time-sharing light irradiating and receiving means. The time-sharing light irradiating and receiving means is a means with a function to identify the measurement location by sequentially irradiating a light from the light source means (light emitting probe) and receiving it at the light-receiving means (light-receiving probe). Specifically, it is a control means for controlling irradiation of the inspection light from the light source means and detection of the light by the detection means in accordance with timing signal generated at specified intervals in a time-sharing manner (Claim 10). More specifically, said control means comprises, as a detection means, an amplifier to output multiple signals sequentially outputted from the light-receiving means as continuous signals, an analog-digital converting means for performing analog-digital conversion of the output from said amplifier and a control means for controlling said detection means, wherein the sampling timing in said analog digital conversion means is controlled by the timing signal from said control means (Claim 11).

In a preferred embodiment, a biomedical optical measurement apparatus of the invention comprises, as a time-sharing light-irradiating and receiving means, aforementioned, analog-digital converting means for performing analog-digital conversion and outputting digitized data of the input signals, a clock means for generating timing signals for said analog-digital converting means to perform analog-digital conversion at a specified sampling timing, a function generating means for generating a function which becomes "0" or "close to 0" near the sampling time of said input signals and a digital multiplying means for multiplying digitized data of input signals output from said analog-digital conversion means by the function from said function generating means, and output the product of the multiplication (Claim 12), and further comprises an integrating means for adding output from the digital multiplying means posterior the digital multiplying means (Claim 13).

According to this biomedical optical measurement apparatus, by selectively employing either a lock-in amplifier or a time-sharing light irradiating and receiving means the scale of circuit and the like can be changed according to individual requirements. Employment of both lock-in amplifier and a time-sharing light irradiating and receiving means assures confident actions and improves reliability. Employment of both of them also ensures easier receiving of light at the light-receiving position closely located from the light source means thereby improving resolution regarding optical measurement.

Further, this invention provides a detection circuit for a biomedical optical measurement apparatus. This detection circuit comprises an analog-digital converting means for performing analog-digital conversion of input signals and outputting digitized data of the input signals, a function generator for generating one or more functions to be selected from trigonometric function, Gaussian function, Hamming and Hanning window functions, a multiplying means for multiplying output from said analog-digital converting means by the function generated from said function generator (Claim 14), and further comprises an adding means for feeding back the sum (results of addition) from itself and adding the sum to the output from said multiplying means (Claim 15).

This detection circuit can be applied to the biomedical optical measurement apparatus of either lock-in amplifier or time-sharing light irradiating and receiving system, and can solve the problem that is associated with phase fluctuations of signals to be detected and common to both systems.

BRIEF DESCRIPTION OF THE DRAWINGS

FIG. 5 is a graph explaining frequency characteristics of a digital low-pass fitter and signals after locked-in;

PREFERRED EMBODIMENT OF THE INVENTION

Embodiments of this invention will be explained hereinafter with the reference of the attached drawings.

Figure 1:
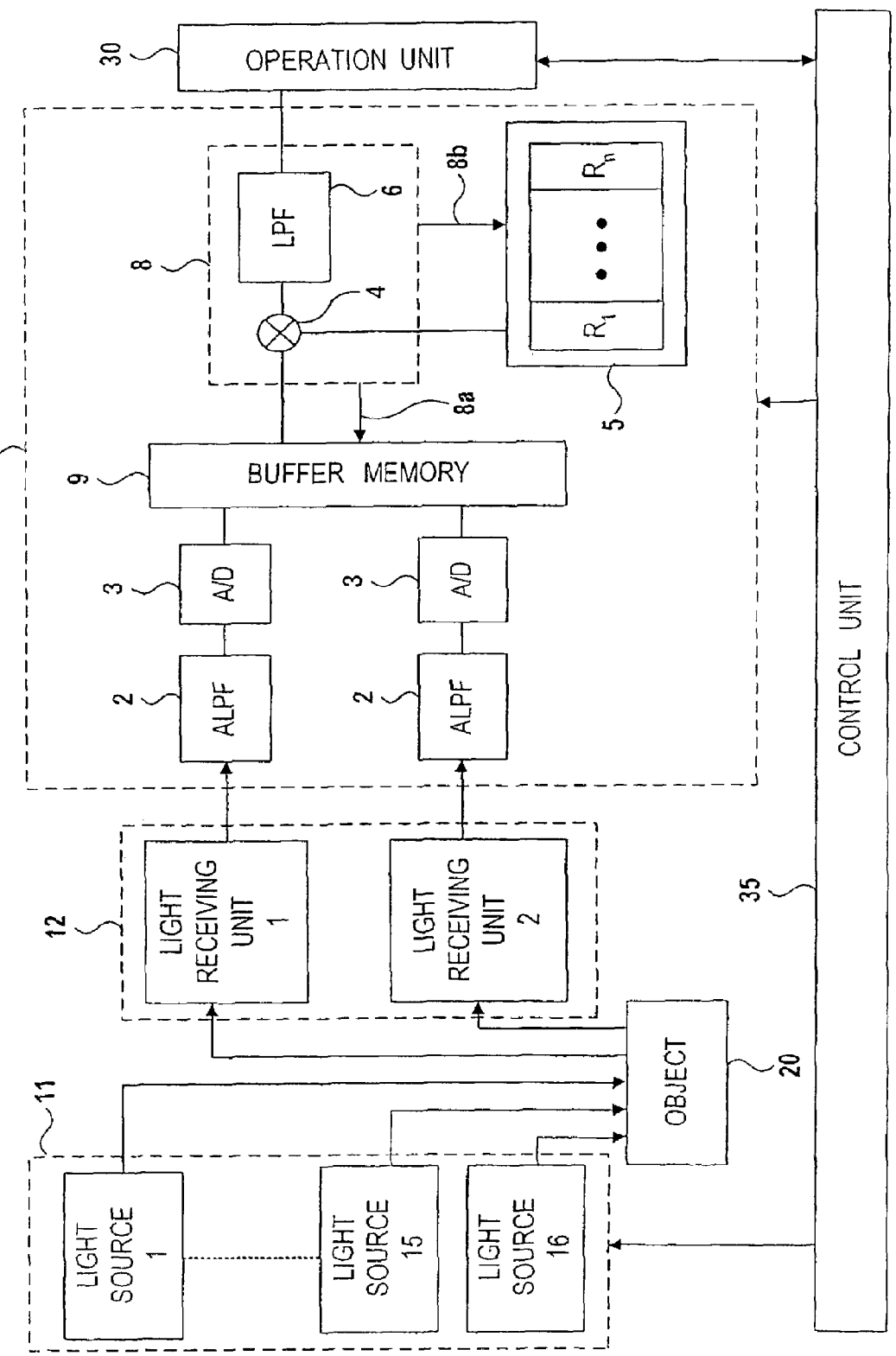
FIG. 1 is a block diagram illustrating the configuration of major components in the first embodiment of a biomedical optical measurement apparatus according to the present invention.
Figure 2:
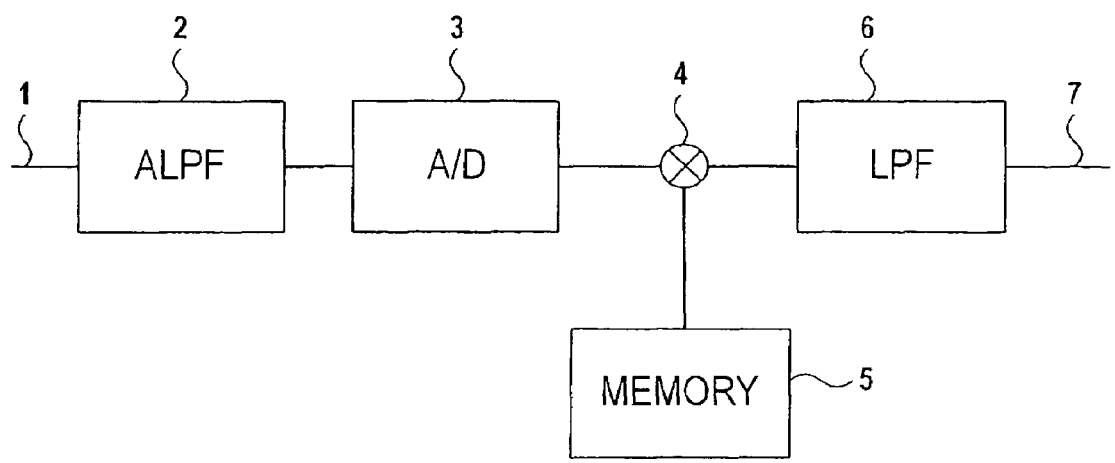
FIG. 2 is a block diagram of a lock-in amplifier in FIG. 1.

FIG. 1 is a block diagram illustrating the configuration of a biomedical optical measurement apparatus according to one embodiment of the present invention, and FIG. 2 is a block diagram showing the configuration of a lock-in amplifier equipped in the measurement apparatus. As shown in these figures, the biomedical optical measurement apparatus comprises a light source unit 11, which generates an inspection light to be irradiated onto an object to be examined 20, a light-receiving unit 12, which receives the light passing through the test object or reflecting near the surface of the object 20 (transmitted light, collectively) and outputs electric signals with intensify corresponding to the received light, an lock-in amplifier 10, which detects the light received at the light-receiving unit 12 in accordance with its frequency, an arithmetic operation unit 30, which input the outputted signals from the lock-in amplifier 10, calculates biomedical information (including hemoglobin concentration) at the inspection light irradiating positions and displays the calculation results, and a control unit 35, which controls the actions of the light source 11, the light-receiving unit 12, the lock-in amplifier 10 and the operation unit 30. Although the arithmetic operation unit 30 and the control unit 35 are separately shown in FIG. 1, both arithmetic operation unit 30 and control unit 35 can be built on a personal computer equipped with an input/output devices such as including display and keyboard.

The light source unit 11 comprises multiple light sources, at each of which the inspection light is modulated by different frequencies. Although a light with a single wavelength can be used as an inspection light, two lights with different wavelengths, for example 780 nm and 830 nm, are usually employed. If the lights with wavelength of 780 nm and 830 nm are modulated with 8 different frequencies, for example, the inspection light will comprise lights modulated at 16 different frequencies.

Sixteen different inspection lights from the light source unit 11 are guided, through optic fibers, for example, to specified inspection positions of the object 20, and irradiated from the surface of the object to the interior of the object, wherein the lights of two different wavelengths are guided as one set of light to one optic fiber. The light passing through the object 20 is guided by the optic fiber placed near the optic fibers for irradiation and received at the light-receiving unit(s) 12. The light-receiving unit 12 outputs an electric signal with an intensity corresponding to that of the received inspection light.

Figure 3A:
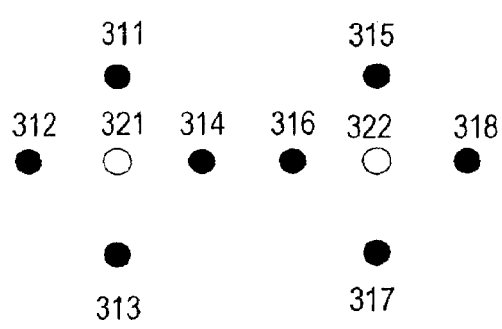
FIG. 3 is a diagram showing an exemplary layout of inspection light irradiating and light-receiving positions in a biomedical optical measurement apparatus.
Figure 3B:
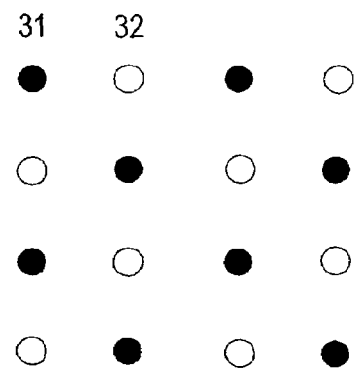

FIG. 3 shows the layout of the light irradiating position 31 and the light-receiving position 32. In the example shown in FIG. 3(A), each of these two light-receiving positions 321 and 322 is surrounded by 4 tips of optic fiber for irradiating light (irradiated positions) 311 to 314 and 315 to 318, respectively. In this layout, because the light-receiving position 32 receives lights with 2 different wavelengths from 4 directions, this position receives 4×2=8 signals. The following explanation concerns the instrument equipped with two light-receiving units 12. However, the number of the light-receiving units 12 needs not be limited to two, and can be varied in accordance with the object. For example, in order to inspect a relatively large area, irradiation positions (shown with ●) 31 and the light-receiving positions (shown with ○) 32 are laid alternately on a matrix. Also in this case, one light-receiving position receives lights with 2 different wavelengths from 2 or 4 directions, namely a composite light which is modulated at maximum 16 different frequencies.

The lock-in amplifier unit 10 receives a synthetic signal made of multiple signals with different frequencies as an input signal, and detects them as individual signals separated by each frequency. The lock-in amplifier unit 10 is equipped with antialiasing low-pass filters (ALPF) 2, A/D converters 3, a reference signal memory 5, a digital lock-in circuit 8 and a buffer memory 9. The input signals are signals with an intensity corresponding to that of light as mentioned previously, so that they contain multiple signals with, for example, 8 different frequencies. They are amplified by the amplifier, which is not shown in the figure. Two sets of an antialiasing low-pass filter 2 and A/D converter 3 are installed in correspondence to two input electric signals.

Figure 4:
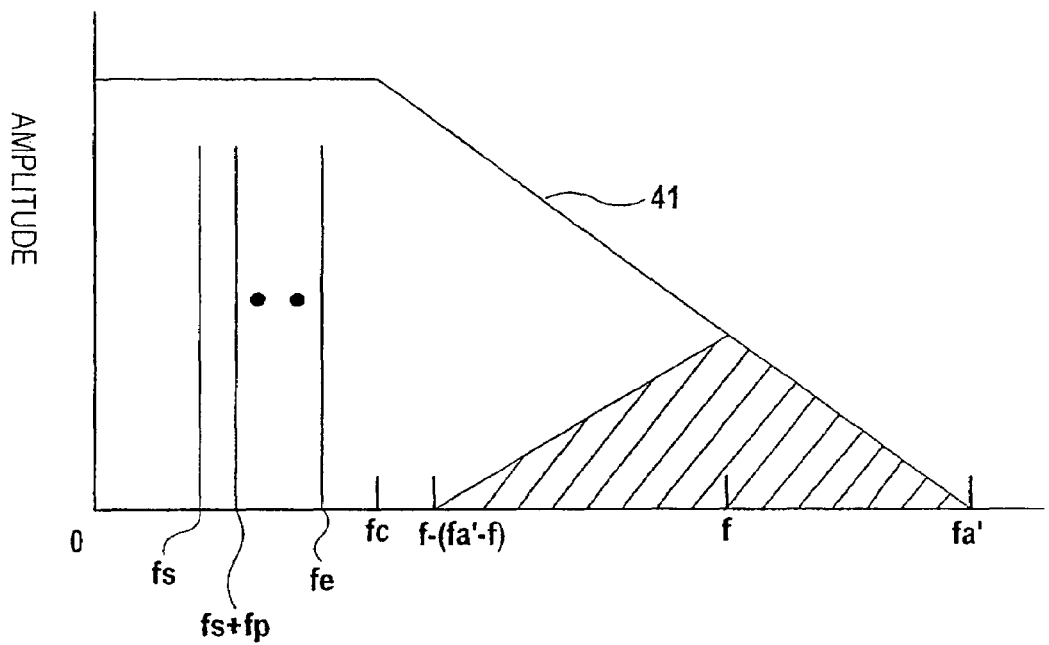
FIG. 4 is a graph explaining the frequency characteristics of an antialiasing low-pass filter and the frequencies of input signals.

The antialiasing low-pass filters 2 attenuate the signals having a frequency higher than that of a reference signal contained in the input signal, particularly the signals that are generated by noise and Nyquist frequency, and output them into the A/D converters. FIG. 4 shows a relationship between frequency characteristics of the antialiasing low-pass filter 2 and frequency of the input signal. In FIG. 4, the waveform 41 shows the frequency characteristics of the antialiasing low-pass filter.

If the frequencies of n+1 signals contained in the input signal are assumed as fs, fs+fp, fs+2fp, ... fe (=fs+n×fp), the cut off frequency fc of the antialiasing low-pass filter 2 is higher than fe (fc>fe). Also, when the attenuation-band frequency of the antialiasing low-pass filter 2 and Nyquist frequency are defined as fa' and f, respectively, the frequency of the signal to be detected is expressed as f−(fa'−f)>fe.

The A/D converters 3 convert analog signals outputted from the antialiasing low-pass filter 2 to digital signals and output them. The buffer memory 9 temporarily stores the data outputted from two sets of A/D converters 3 and outputs them into the digital lock-in circuit 8.

The digital lock-in circuit 8 is equipped with a multiplier 4, a low-pass filter 6 and a control unit (not shown in the figure). The digital multiplier 4 sequentially multiplies digitized data of the input signals outputted from the A/D converters 3 by digitized data of the reference data readout sequentially from the reference signal memory 5, and outputs the multiplied signals into the digital low-pass filter 6.

The reference signal memory 5 pre-stores digitized data of multiple reference signals R1 to Rn, for example, digitized data of the reference signals with 16 different frequencies which correspond to those of the input signal. If the frequencies to be used for modulation are changed at the light source unit 11, the data in the reference signal memory 5 are re-written and digitized data of the reference signals with new frequencies are stored.

Figure 5:
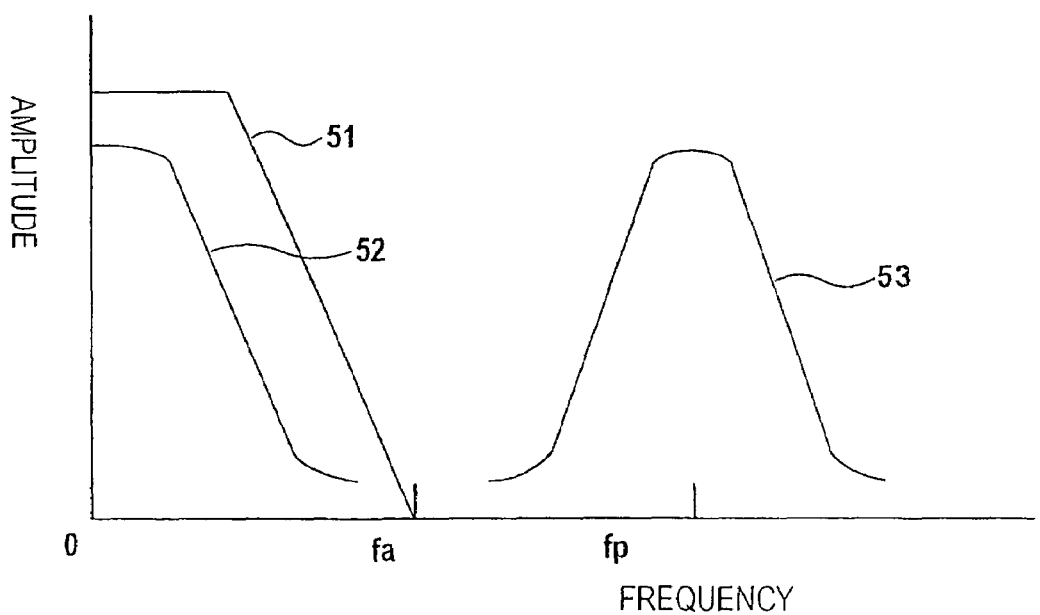

The digital low-pass filter 6 takes out the DC component from the multiplied signals outputted from the digital multiplier 4, and outputs it as an output signal 7 in the operation unit 30. FIG. 5 shows a relationship between the frequency characteristics of the digital low-pass filter 6 and the signals after locked-in. In FIG. 5, the waveform 51 shows the frequency characteristics of the digital low-pass filter 6, while the signals 52 and 53 show the waveform after locked-in by the digital multiplier 4. When the digital low-pass filter 6 takes DC data out from the signals 52 and 53 locked-in the digital multiplier 4, since an attenuation-band frequency fa is set for the digital low-pass filter 6 as shown in FIG. 5, the signal 53 (signal other than the signal 52) after locked-in by digital multiplier 4 has a center frequency fp and the frequency pitch between signal 52 and the other signal 53 after lock-in becomes fp. The relationship between the attenuation-band frequency fa of the digital low-pass filter and the center frequency fp of the other signal 53 after lock-in satisfies fp≧2fa. All other signals to be detected should mutually have the frequency pitch of fp. This is to obtain a necessary amount of attenuation of noise and other signals for a signal to be locked-in.

The digital lock-in circuit 8 (digital multiplier 4, digital low-pass filter 6 and the like) may consist of electronic components such as digital signal processor (DSP)).

Actions of the lock-in amplifier 10 having such configuration are explained. First, the control circuit in the digital lock-in circuit 8 transmits a control signal 8a to the buffer memory 9, reads out either of the data witch are outputted from 2 sets of A/D converters 3 and stored in the buffer memory 9. It also transmits a control signal 8b to the reference signal memory 5 and sequentially reads out digitized data of reference signals stored in the reference signal memory 5. The digital multiplier 4 sequentially multiplies the data read out from the buffer memory 9 by digital data of reference signals sequentially read out from the reference signal memory 5 and outputs the results of multiplication. The digital low-pass filter 6 takes out the DC data from the output of the digital multiplier 4, and outputs them as an output signal.

According to this embodiment of this invention, by storing digitized data of multiple reference signals in the reference signal memory 5 it becomes unnecessary to provide the reference signal generating circuits in a number equal to the number of frequencies to be detected as in the conventional embodiment. One of the examples is that one digital lock-in circuit can serve as 16 analog lock-in amplifiers required for conventional configurations. Moreover, as digitized reference signals with new frequencies can be stored only by re-writing the data stored in the reference signal memory 5, it becomes easier to deal with changes in frequencies.

This embodiment of the invention has been explained with the case in which a pair of lights each having light different wavelength is modulated with 8 different frequencies. However, this invention is not limited to this embodiment, and can be applied to the case in which two or more lights with one or more different wavelengths are modulated by tow or more frequencies. The light-receiving unit 12 has been described with the case in which two signals are to be detected, but the number of signals to be detected is not limited to two.

Further, while one digital lock-in circuit 8 sequentially processes multiple reference signals with different frequencies in this embodiment, it is possible to install one processing circuit for each modulation frequency. Such embodiments are explained hereinafter with reference to FIGS. 6 to 10.

Figure 6:
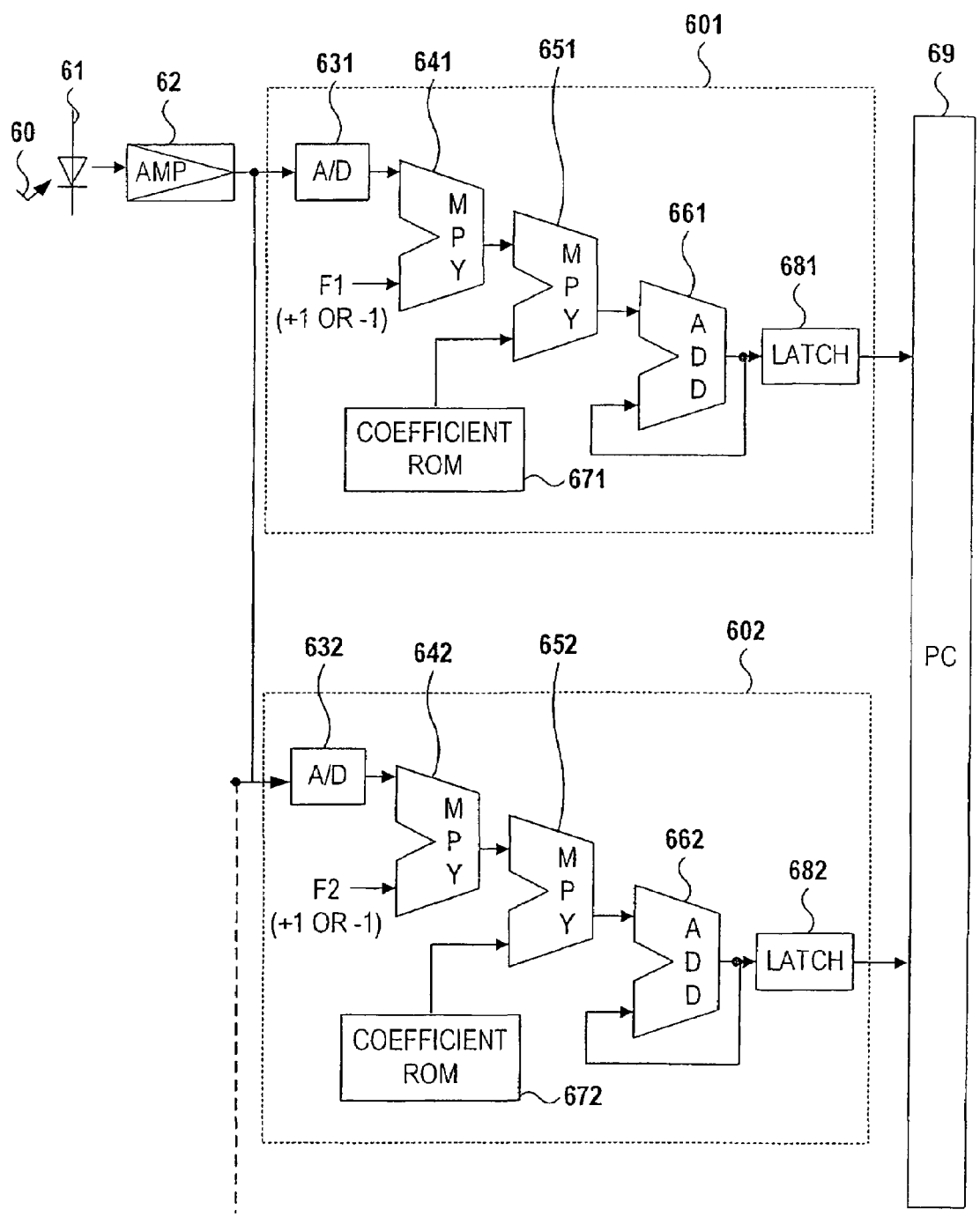
FIG. 6 is a block diagram showing the configuration of a lock-in amplifier used in the biomedical optical measurement apparatus according to the second embodiment of the present invention.

FIG. 6 shows a block diagram of a lock-in amplifier to be used in the biomedical optical measurement apparatus according to the second embodiment of this invention. Also in this second embodiment, an inspection light 60 passing through the object is received by a light-receiving element (diode) 61, converted photoelectrically and outputted as a signal with an intensity corresponding to that of the light into the amplifier 62, as in the embodiment shown in FIGS. 1 and 2. In this embodiment, the signals amplified by the amplifier 62 are inputted in digital lock-in circuits 601, 602 . . . which are installed at every frequency component. The input signal is a synthesized signal made of multiple signals with different frequencies. While only digital processing circuits 601 and 602 in 2 systems are shown in the figures, the digital circuits of similar configuration can be installed in a number equal to the number of frequencies (n) of the signals to be detected. As the configuration of every digital lock-in circulation 601 is similar except for the reference signal to be used, one digital lock-in circuit 601 will be explained.

The digital lock-in circuit 601 constitutes a digital lock-in amplifier having an A/D converter 631, two digital multipliers 641 and 651 and an adder 661. Posterior the adder, there is provided a latch circuit 681 for latching output signals from each digital lock-in circuit 601 and inputting them into the operation unit 69.

The A/D converter 631 converts the output from the amplifier 62 and outputs it to the digital multiplier 641. The digital multiplier 641 multiplies the output from the A/D converter 631 by the reference signal F1, and outputs the result of the multiplication into the following digital multiplier 651. Specifically, the digital multiplier 641 multiplies input signals by +1 or −1 according to the frequency of the reference signal F1. Digitized data of the reference signal to be used in the digital multiplier 641 is stored, as in the embodiment illustrated in FIG. 1, in the reference signal memory not illustrated in the figure.

The digital multiplier 651 multiplies the output from the digital multiplier 641 by a low-pass filter coefficient stored in the coefficient ROM 671, and outputs the result of the multiplication into the following digital adder 661. The digital adder 661 sequentially adds the output from the digital multiplier 651 and the sum fedback from the adder itself, processes it to take out a DC component and outputs into the latch circuit 681.

Filtering processing by this digital multiplier 651 and the digital adder 661 is similar to the processing by the digital low-pass filter 6 in the embodiment shown in FIG. 1 (FIG. 2), with the frequency characteristics being similar to what is shown in FIG. 5.

The latch circuit 681 latches signals which are subjected to filtering processing by the digital multiplier 651 and the digital adder 661, and outputs them in the operation unit (PC) 69.

Figure 7:
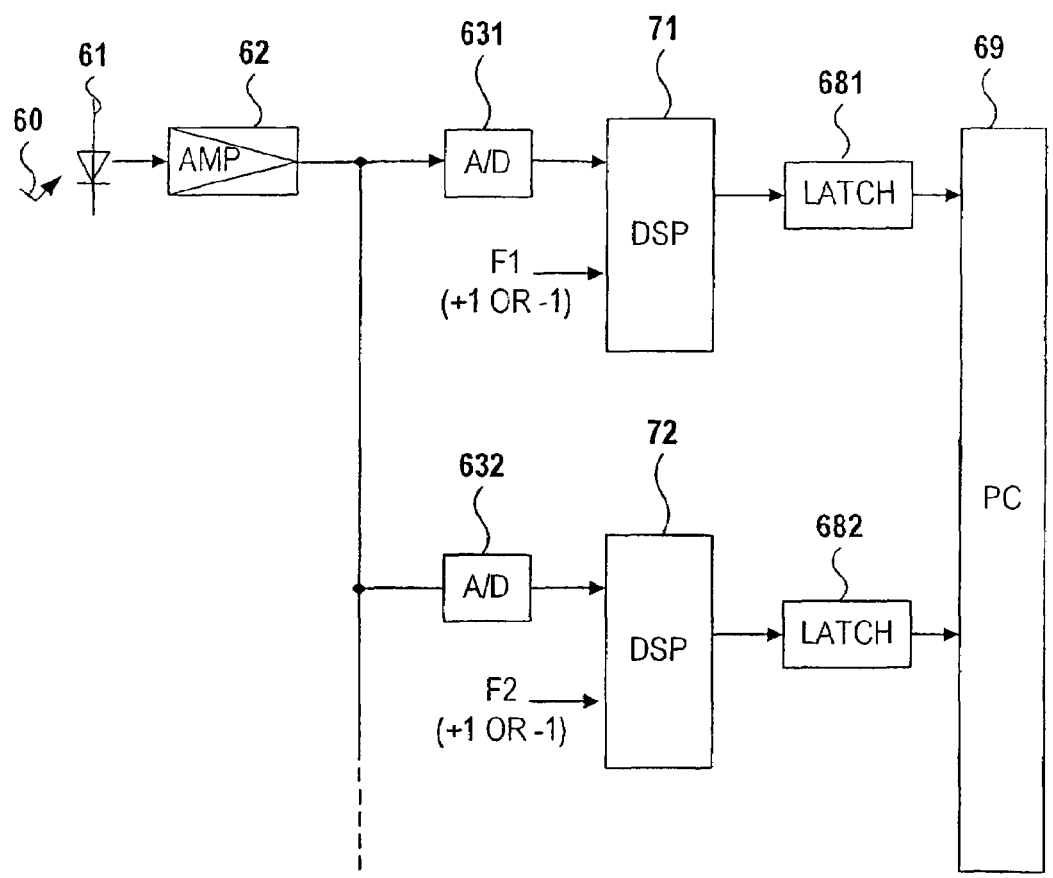
FIG. 7 is a block diagram showing the configuration of a variant of the lock-in amplifier in FIG. 6.

FIG. 7 is a block diagram showing a variant of the lock-in amplifier shown in FIG. 6. Since components of the lock-in amplifier in FIG. 7 with the same configuration as those in FIG. 6 are marked with the same symbols, explanation thereof is excluded. This lock-in amplifier is different from that in FIG. 6 in that the digital multipliers 641, 642, 651 and 652 and the digital adders 661 and 662 in FIG. 6 are replaced by the digital signal processors (DSP) 71 and 72.

Figure 8:
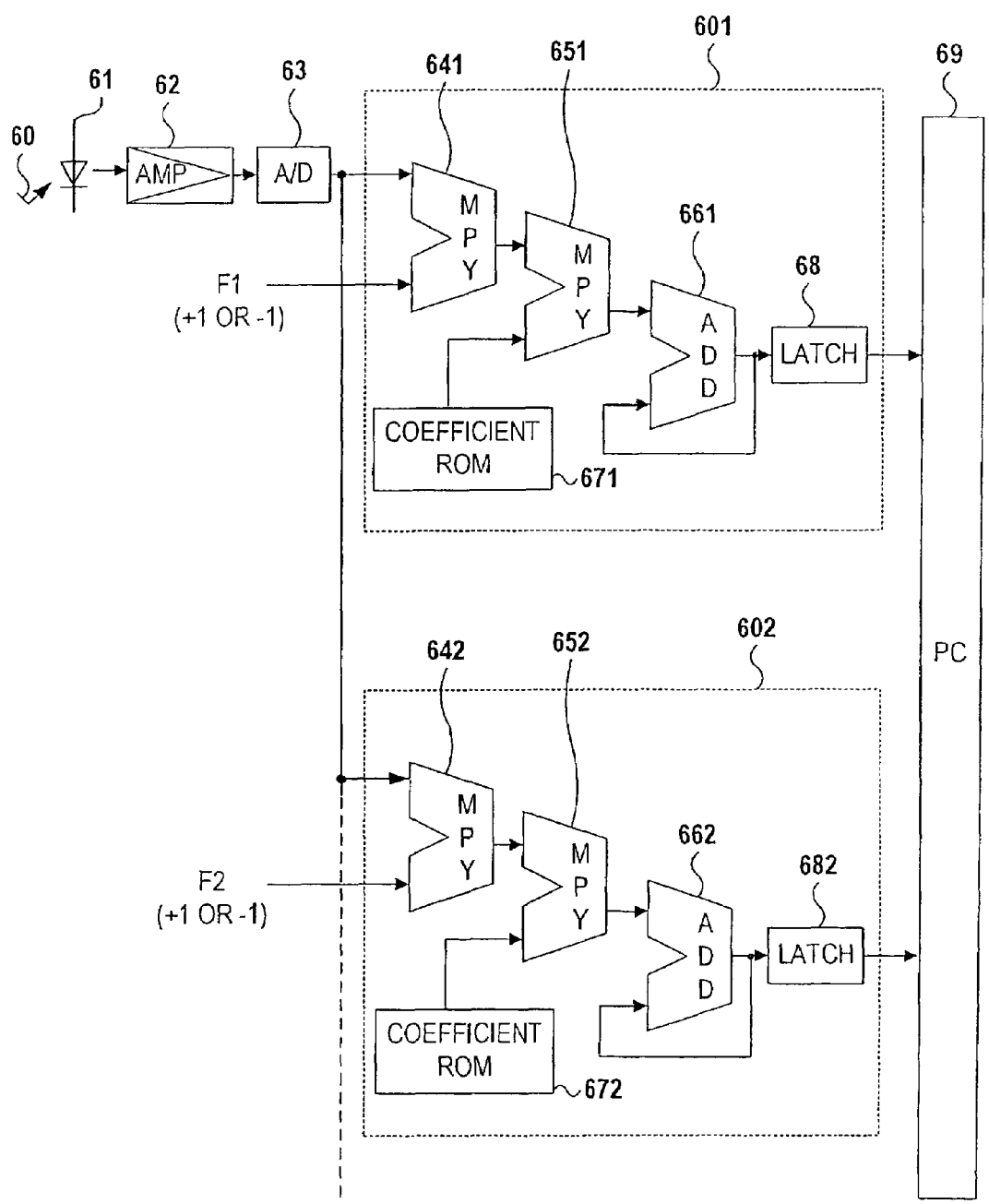
FIG. 8 is a block diagram showing the configuration of another variant of the lock-in amplifier in FIG. 6.

FIG. 8 is a block diagram showing another variant of the lock-in amplifier shown in FIG. 6. Since components of the lock-in amplifier in FIG. 8 with the same configuration as those in FIG. 6 are marked with the same symbols, explanation is thereof excluded. This lock-in amplifier is different from that in FIG. 8 in that the analog/digital conversion is performed by one A/D converter 63. Specifically, in the lock-in amplifier in FIG. 6 the output from the amplifier 62 is subjected to analog/digital conversion by the A/D converters 631 and 632 installed prior to each digital lock-in circuit 601 and 602, respectively, whereas in the lock-in amplifier in FIG. 8 the output from the amplifier 62 is subjected to analog/digital conversion by one A/D converter 63 and the output from the A/D converter 63 is then inputted into each digital lock-in circuit 601 and 602, which comprise the digital multipliers 641, 642, 651 and 652, and the digital adders 661 and 662.

Figure 9:
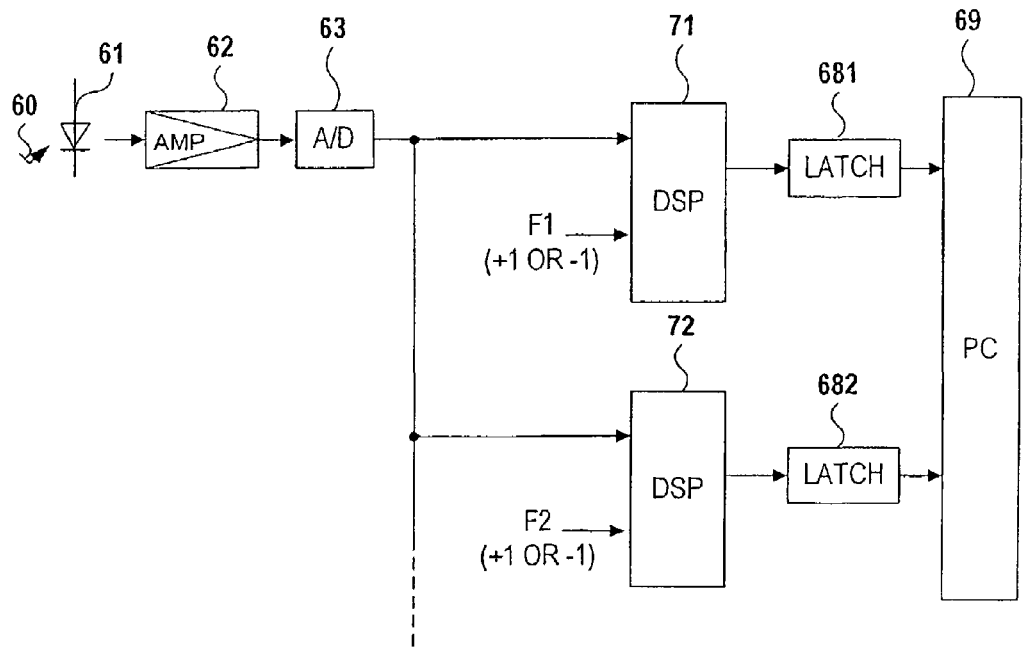
FIG. 9 is a block diagram showing the configuration of a variant of the lock-in amplifier in FIG. 7.

FIG. 9 is a block diagram for another variant of the lock-in amplifier shown in FIG. 7. Since components of the lock-in amplifier in FIG. 9 having the same configuration as those in FIG. 7 are marked with the same symbols, explanation thereof is excluded. The lock-in amplifier shown in FIG. 9 is different from that in FIG. 7 in that a single A/D converter 63 is used for analog-digital conversion in the lock-in amplifier in FIG. 9.

Figure 10:
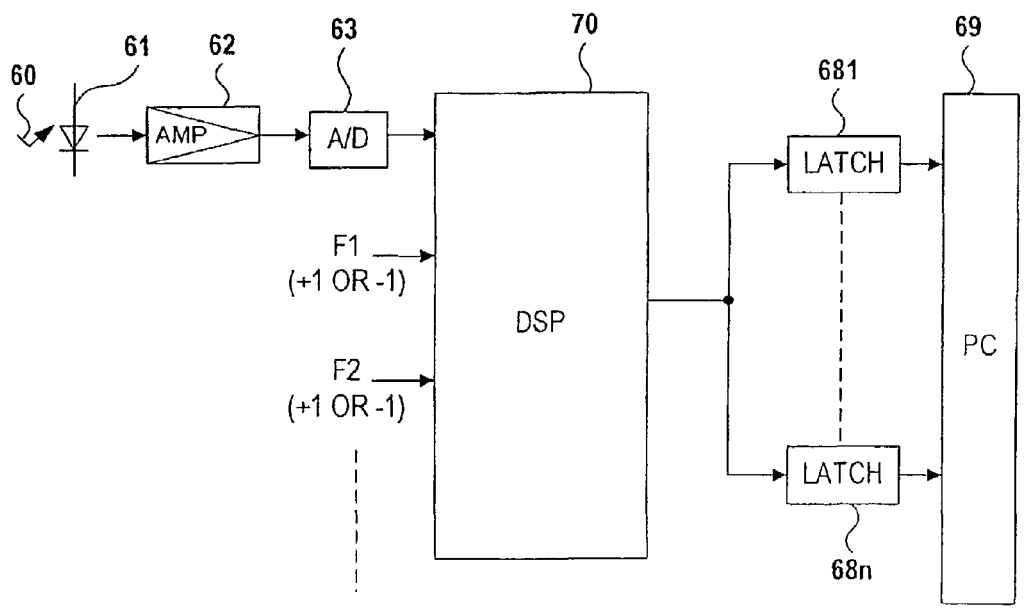
FIG. 10 is a block diagram showing the configuration of a variant of the lock-in amplifier in FIG. 9.

FIG. 10 is a block diagram for another variant of the lock-in amplifier shown in FIG. 9. Since components of the lock-in amplifier in FIG. 10 having the same configuration as those in FIG. 9 are marked with the same symbols, explanation is thereof excluded. The lock-in amplifier shown in FIG. 10 is different from that in FIG. 9 in that the lock-in amplifier in FIG. 10 uses the digital signal processor (DAP) 70 for digital signal processing, and the results are latched in multiple latch circuits 681 to 68n. This configuration (variation) is similar to the variant of the embodiment in FIG. 1, in which a digital lock-in circuit 8 (digital multiplier 4, digital low-pass filter 6, and like) is replaced by a digital signal processor (DSP).

As mentioned above, there can be various configurations of the lock-in amplifier to be employed in the biomedical optical measurement apparatus of this invention as shown in FIGS. 6 to 10. It is desirable to employ optimal circuits in view of the purpose of use and the scale of circuit.

Figure 11:
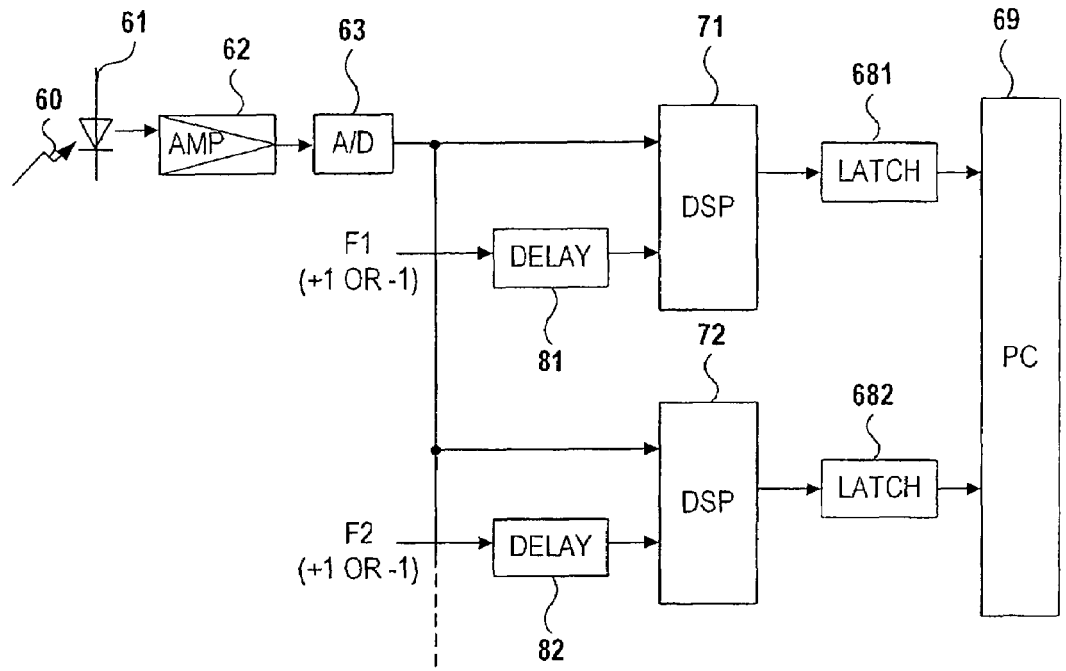
FIG. 11 is a block diagram showing the configuration of an improved lock-in amplifier in FIG. 6.
Figure 15:
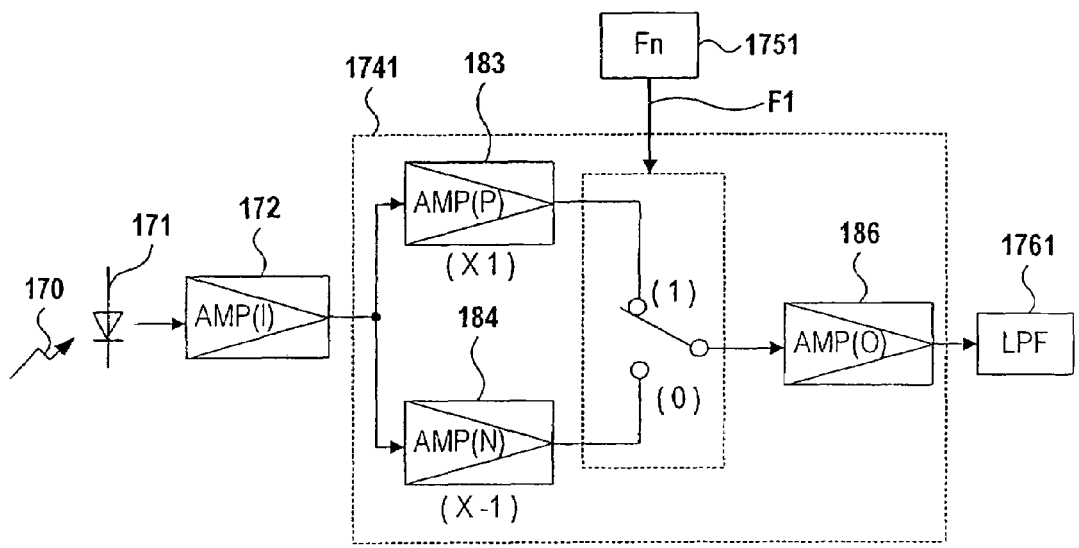
FIG. 15 is a block diagram showing the detailed configuration of the lock-in amplifier in FIG. 14.

Next, as another embodiment of this invention, there will be explained configuration of a lock-in amplifier having means for correcting phase difference when the signal to be detected has phase difference from the reference signal. The means for correcting such phase difference can be applied to all lock-in amplifiers illustrated in FIGS. 6 to 11 mentioned above. An example in which the correction means is applied to the lock-in amplifier in FIG. 9 is shown in FIG. 11. Components of the lock-in amplifier in FIG. 11 having the same configuration as those that in FIG. 9 are marked with the same symbols and explanation thereof is excluded.

Figure 17A:
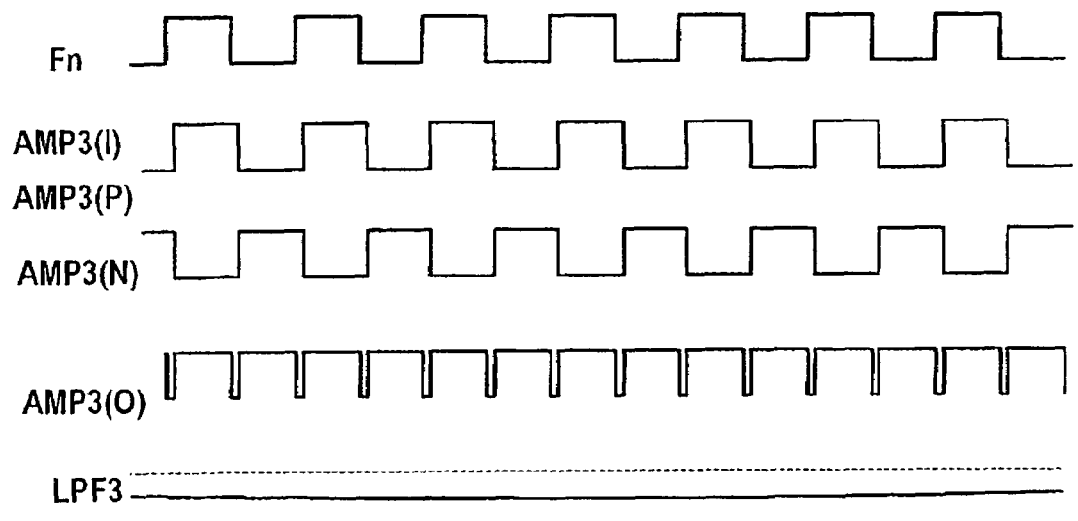
FIG. 17 is a timing chart showing signal waveforms to explain the actions of the lock-in amplifier in FIG. 14, in cases that the signal to be detected have phase difference from that of reference signal and that the phase difference changes.
Figure 17B:
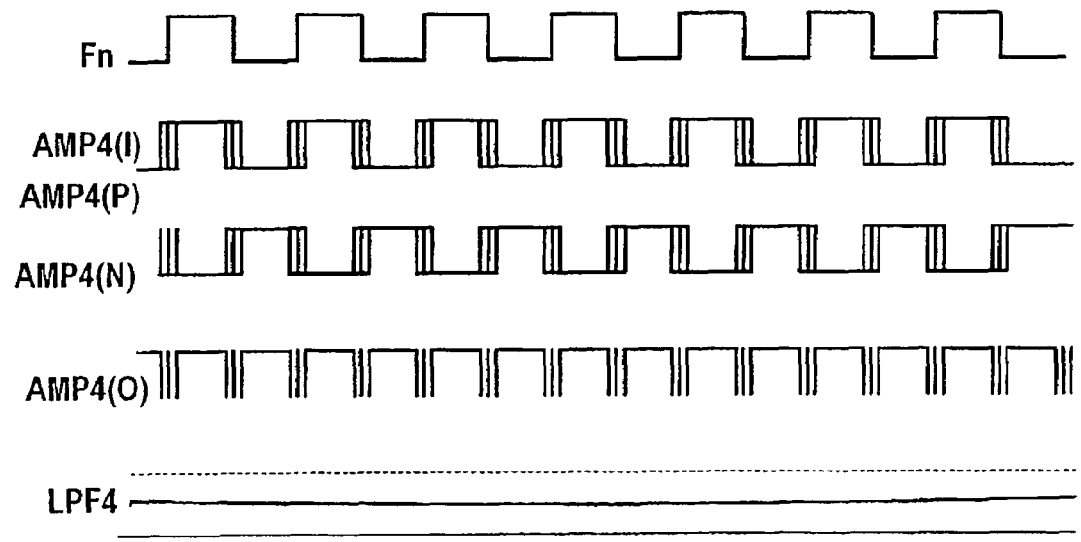

The lock-in amplifier in FIG. 11 is different from that in FIG. 9 in that reference signals F1 and F2 are supplied to the digital signal processors (DSP) 71 and 72 through the delay circuits (DELAY) 81 and 82 in the lock-in amplifiers in FIG. 11. By installing these delay circuits 81 and 82, the reference signals F1 and F2 can be supplied to the digital signal processors (DSP) 71 and 72 after correcting phase difference if the signals to be detected have phase difference from that of the reference signal Fn. Delaying reference signals in accordance with phase difference can prevent the decline in the level of detection signal by the phase difference as shown in FIG. 17(A) and ensures a sufficiently large S/N ratio.

Figure 12A:
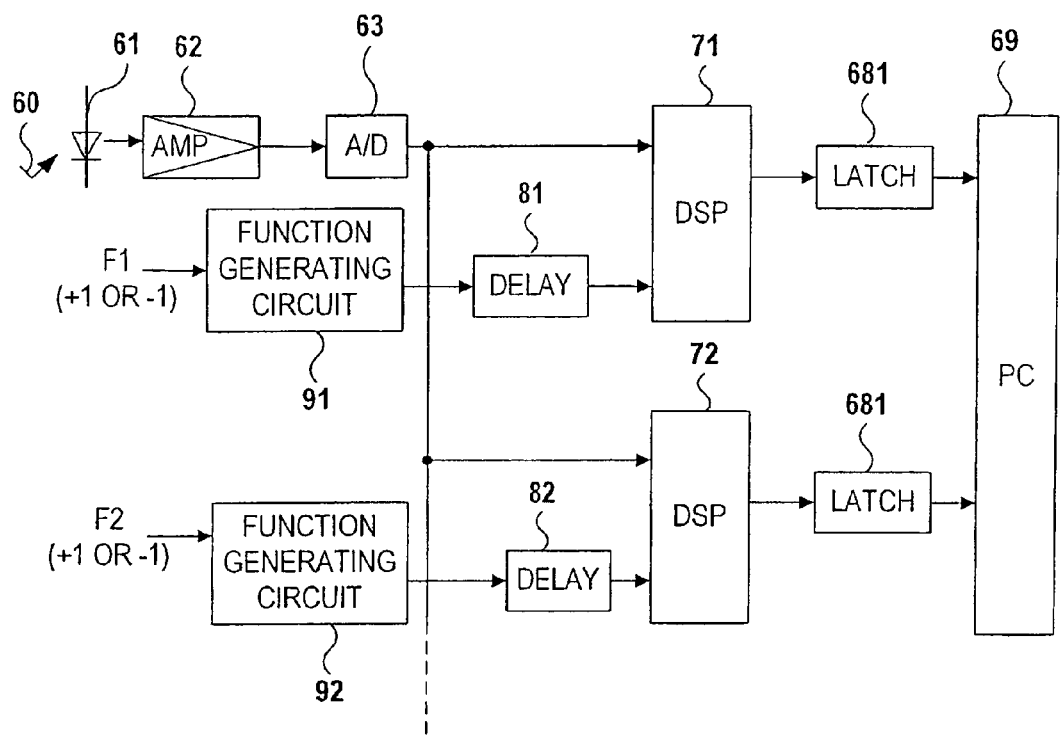
FIG. 12 is a block diagram showing the configuration of a further improved lock-in amplifier in FIG. 6.

Next, as yet another embodiment of this invention, the configuration of a lock-in amplifier having a means for preventing declining of signal due to changes in phase difference between signals to be detected and reference signals. Such means can be applied to all lock-in amplifiers shown in FIGS. 6 to 11 mentioned above. An example of such means applied to the lock-in amplifier of FIG. 11 is shown in FIG. 12. Components of the lock-in amplifier in FIG. 12 having the same configuration as those in FIG. 11 are marked with the same symbols and explanation thereof is excluded.

As illustrated, the lock-in amplifiers of this embodiment is equipped with function generating circuits 91 and 92, which generate specified function waveforms in accordance with reference signals Fn (F1, F2 . . . ) to be supplied to the digital signal processors (DSP) 71 and 72 through the delay circuits (DELAY) 81 and 82. In order to obtain a signal which certainly synchronize with reference signal Fn by multiplying the signal to be detected by the function, the function Mn should have a function waveform which becomes "0" or "close to 0" near the level changing point of the reference signal Fn. These functions include trigonometric function, Gaussian function or Window Function, such as Hamming or Hanning window functions.

Figure 12B:
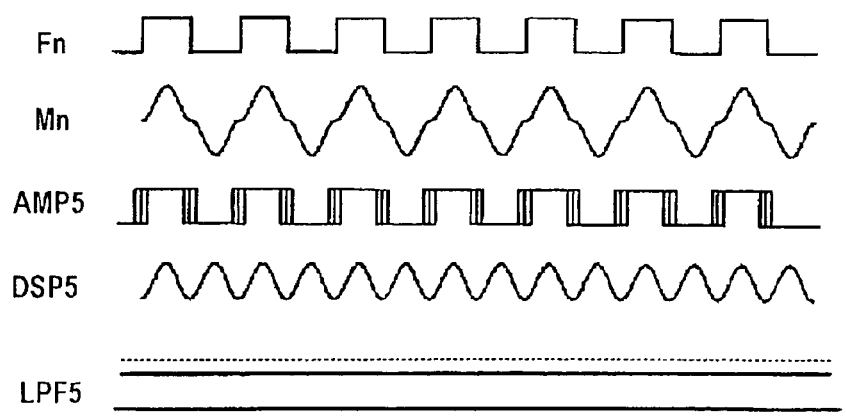

The relationship between the reference signal Fn, function Mn and a signal to be detected AMP5 is shown in FIG. 12(B). As illustrated in the figure, phase difference between the signal to be detected AMP6 and the reference signal Fn generally changes in the area where the level of the reference signal Fn changes from "0" to "1" or from "1", to "0", or near the level changing point. Accordingly, the function Mn, whose function waveform becomes "0" or "close to 0" near the level changing point of the reference signal Fn is generated in accordance with the reference signal Fn, and the signal to be detected AMP5 is multiplied by the function to produce a multiplication waveform DSP5 using digital signal processors 71 and 72. Then this multiplication waveform DSP5 is subjected to filtering processing to obtain a detection signal LPF5. By this, the level of detection signal LPF5 will not change and becomes relatively stable, even if the phase of the signal AMP5 changes as a waveform shown in FIG. 12(B). Delay circuits 81 and 82 shown in FIG. 12(A) can be excluded when no certain phase difference exists between signals to be detected and reference signals.

The embodiments and variants of the lock-in amplifier unit in the biomedical optical measurement apparatus equipped with a lock-in amplifier have been explained above. According to this biomedical optical measurement apparatus, by constructing a lock-in amplifier with a digital circuit and by equipping a reference signal memory which stores multiple reference signals with different frequencies as digitized data, the installation of reference signal generating circuits in a number equal to that of frequencies of the signals to be detected becomes unnecessary and the data can be rewritten easily when the frequencies are changed. Moreover, the installation of a delay circuit or function generating circuit at the reference signal input side of the lock-in amplifier prevents decline of signals and ensures stable measurement even if there occurs a phase difference between a reference signal and a signal to be detected and the phase difference changes.

Figure 18A:
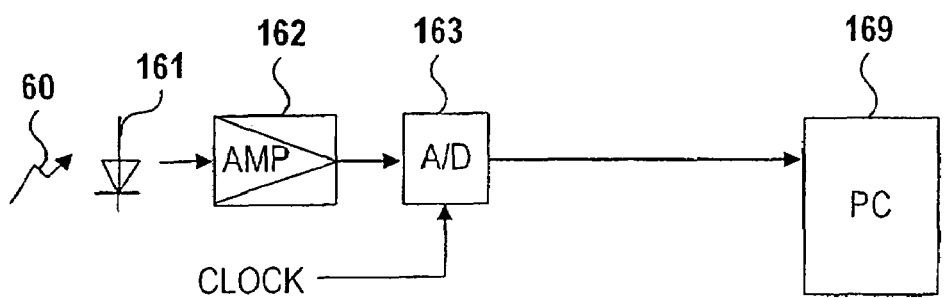
FIG. 18 is a drawing showing a prior art biomedical optical measurement apparatus equipped with a time-sharing light irradiating and receiving means.
Figure 18B:
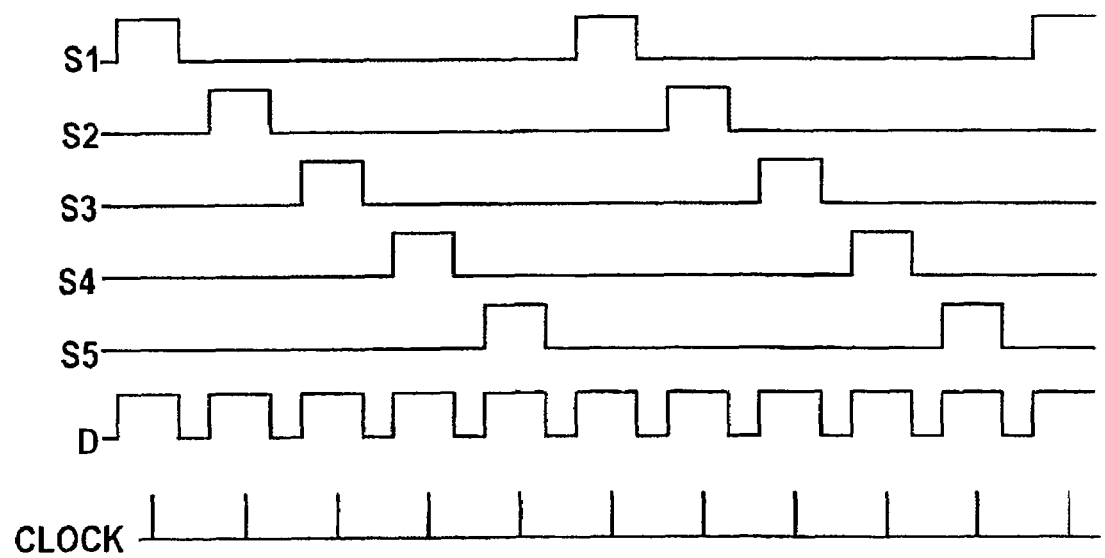
Figure 19A:
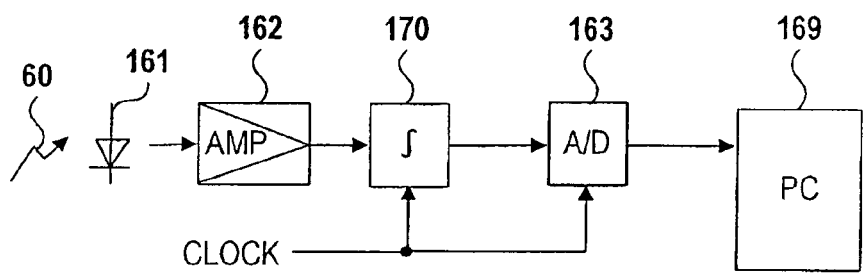
FIG. 19 is a drawing showing another biomedical optical measurement apparatus to which improvements are given to the biomedical optical measurement apparatus in FIG. 18 for increasing the S/N ratio.

The biomedical optical measurement apparatus in these embodiments can be applied to the biomedical optical measurement apparatus equipped with, for example, conventional time-sharing light irradiating and receiving function as shown in FIG. 18 or 19. While a digital lock-in amplifier unit having the same configuration as those shown in FIG. 1 mentioned above or FIGS. 6 to 12 is installed, in addition to the digital lock-in amplifier unit 10, the measurement apparatus is equipped with, as a detection means, the amplifier 162 which sequentially outputs multiple signals outputted from the light-receiving element 161 as continuous signals, and the analog digital converter 163, which performs analog/digital conversion of the output from the amplifier 162. Irradiation of an inspection light from the light source unit is performed in time-sharing manner in accordance with a timing signal from the control unit 35 (FIG. 1), and the sampling timing in the analog-digital converter 163 is controlled so as to synchronize with this timing signal.

Next, another embodiment of this invention is explained. This embodiment is applied to the biomedical optical measurement apparatus, which is equipped with a time-sharing light irradiating and receiving means instead of, or in addition to, the aforementioned lock-in amplifier. The time-sharing light irradiating and receiving means has a function of sequentially irradiating light from the light source unit (light emitting probe), receiving the light at the light-receiving unit (light-receiving probe) to identify the measurement position. Namely, the biomedical optical measurement apparatus equipped with a time-sharing light irradiating and receiving means sequentially irradiates light from each light source at the light source unit in a time-sharing manner, and detects only signals with a specific timing from the lights detected at the light-receiving position, whereas the biomedical optical measurement apparatus in FIG. 1 continuously irradiate the light with multiple frequencies from each light source at the light source unit 11, and detects the light with specified frequency from the lights with multiple frequencies detected at the light-receiving position, by using a lock-in amplifier.

Figure 13A:
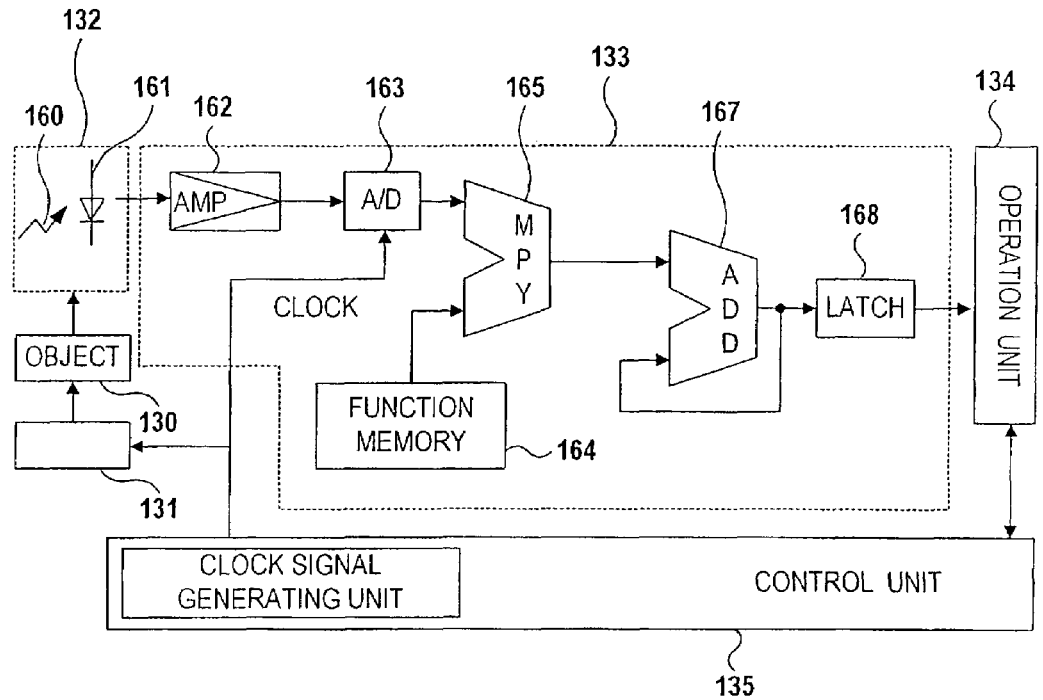
FIG. 13 is a diagram representing an example of a biomedical optical measurement apparatus, which can cope with phase changes at accelerated sampling frequency.
Figure 13B:
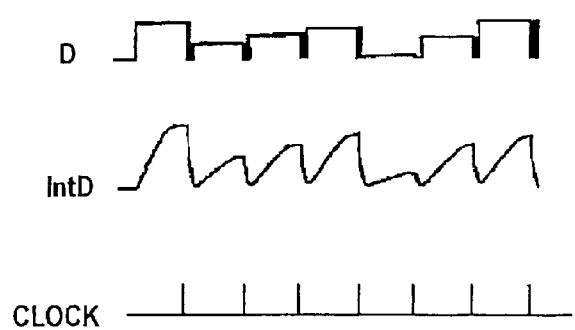
Figure 14:
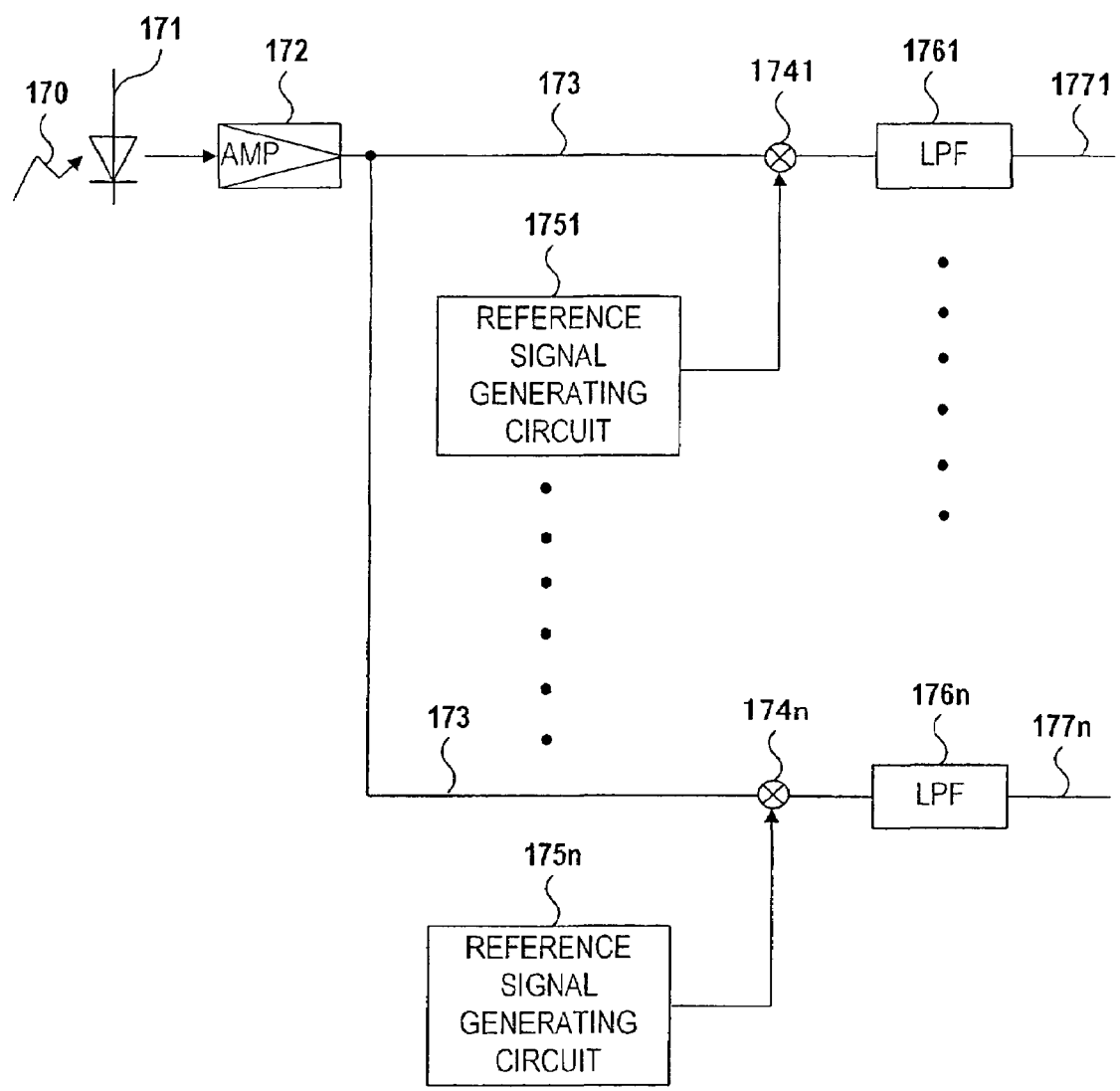
FIG. 14 is a block diagram showing a lock-in amplifier of a conventional biomedical optical measurement apparatus.
Figure 16A:
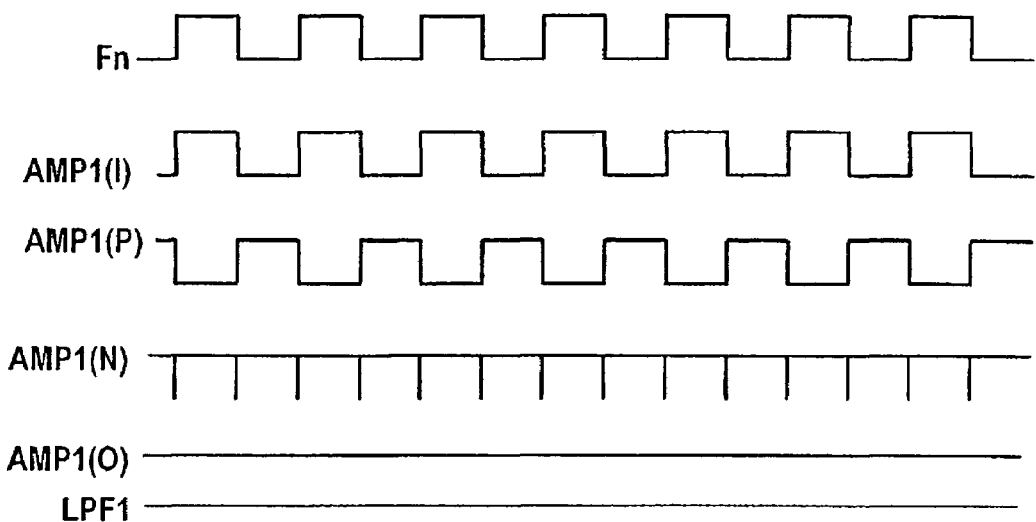
FIG. 16 is a timing chart showing signal waveforms to explain the actions of the lock-in amplifier in FIG. 15.
Figure 16B:
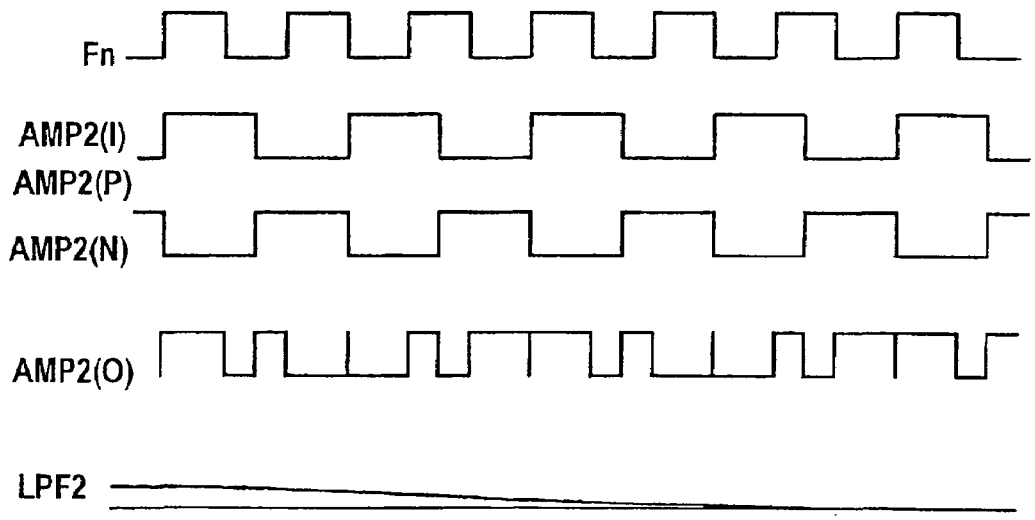

An embodiment of the biomedical optical measurement apparatus equipped with a time-sharing light irradiating and receiving means is shown in FIG. 13. This biomedical optical measurement apparatus is equipped with the light source unit 131, which sequentially generates multiple inspection lights to be irradiated onto multiple positions of an object to be examined 130 in a time-sharing manner, the light-receiving unit 132, which receives light passing through the object 130 and outputs electric signals with an intensity corresponding to that of light, time-sharing detection unit 133, which detects the light received at the light-receiving unit 132, the arithmetic operation unit 134, which input signals outputted from the time-shared detection unit 133, calculates biomedical information (for example, hemoglobin concentration and like.) at the inspection light irradiation position and displays the calculation results, and the control unit 135, which controls actions at the light source unit 131, the light-receiving unit 132 and the time-sharing detection unit 133. Further, while the operation unit 134 and the control unit 135 are shown separately in the embodiment illustrated in the figure, they can be constructed on a PC equipped with I/O devices, such as display and keyboard, as in the biomedical optical measurement apparatus shown in FIG. 1.

The light source unit 131 and the light-receiving unit 132 are configured, though simplified in the Figure, as illustrated in FIG. 3 for example, so as to irradiate the inspection light from multiple irradiation positions onto the surface of an object to be examined and receive the light (inspection light) at multiple light-receiving positions laid out on the designated positions associated with the irradiation positions. The light source unit 131 irradiates a light with a specified frequency on different irradiation positions at certain time intervals by using a clock signal generated at the clock signal generator of the control unit 135. The light-receiving unit 132 comprises multiple light-receiving elements or optic fibers each end of which is connected with a light-receiving element. The inspection light 160 received by each light-receiving element is outputted into the same amplifier 162.

The time-sharing detection unit 133 is equipped with the amplifier 162, an A/D converter 163 which performs analog/digital conversion of the signals amplified by the amplifier 162, a digital multiplier 165 for multiplying output from the A/D converter 163 by a specified function, a function memory 164, which stores functions to be used by the digital multiplier 165, a digital adder 167 which integrates output from the digital multiplier 165, and a latch circuit 168 which latches output from the digital adder 167.

Also in this biomedical optical measurement apparatus signals S1 to S5 with corresponding intensity to that of light and outputted from the light-receiving element 161 are amplified by the amplifier 162 and inputted as a signal D into the A/D converter 163, as in the biomedical optical measurement apparatus referred to in FIG. 18. The A/D converter 163 performs A/D conversion of the output from the amplifier 162 at a sampling time synchronized with a clock signal CLOCK, and outputs them into the digital multiplier 165. The function memory 164 contains a function, which becomes "0" or "close to 0" near the sampling timing, for example, trigonometric function, Gaussian function or window functions, such as Hamming and Hanning functions. These functions are similar to those generated by the function generating circuits 91 and 91, which are employed in the lock-in amplifier in FIG. 12. The multiplier 165 reads the aforementioned specific function from the function memory 164, multiplies the output from the A/D converter 163 by the function and outputs the product of the multiplication into the following digital adder 167.

The digital adder 167 sequentially adds the output from the digital multiplier 165 and the sum fedback from itself, performs integration processing, and outputs the integrated signals into the latch circuit 168. Processing by the digital adder 167 is reset at the time synchronized with the clock signal CLOCK. The latch circuit 168 latches the signals integrated by the digital adder 167 with the sampling timing (CLOCK), and outputs them into the operation unit (PC) 134.

Figure 19B:
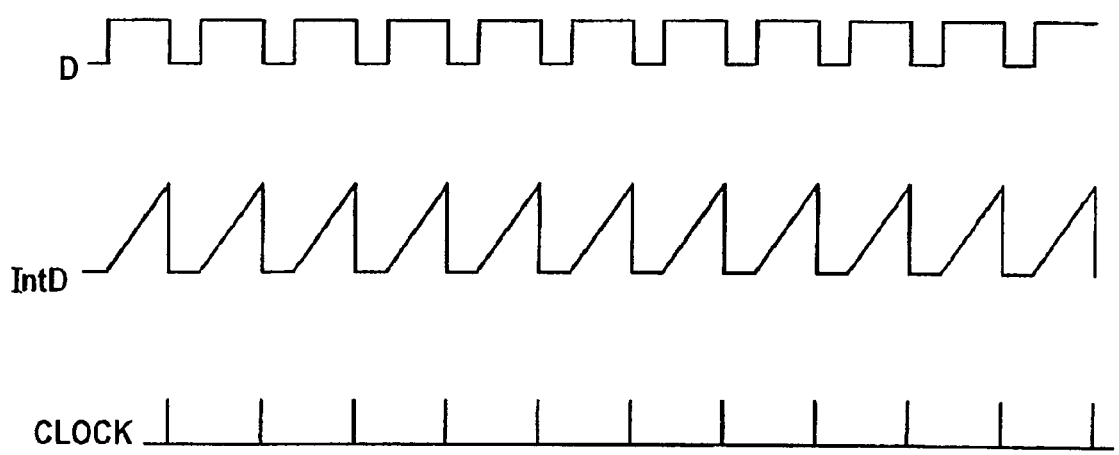
Figure 20A:
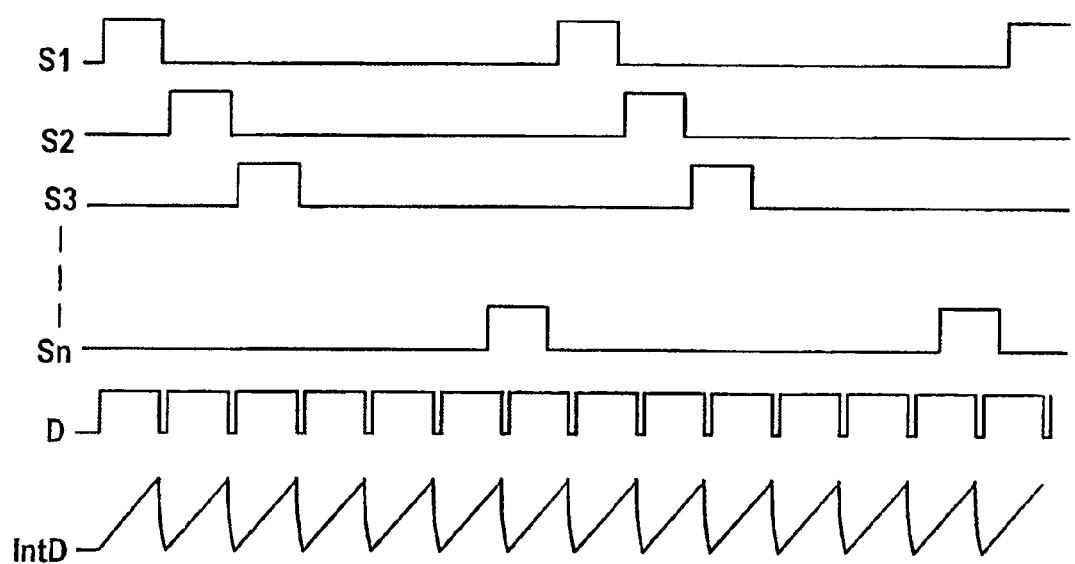
FIG. 20 is a drawing showing an example in which the sampling frequency in a biomedical optical measurement apparatus in FIG. 19 is accelerated.
Figure 20B:
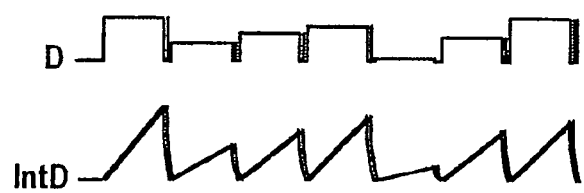

According to the biomedical optical measurement apparatus of this embodiment, by multiplying the output from the A/D converter 163 by the function, which becomes "0" or "close to 0" near the sampling timing, the level of detection signal IntD becomes unchanged even the phase changes as shown in the waveform D referred to in FIG. 19(B), thereby preventing the error attributable to the phase change.

As an embodiment of this invention, the improvement to the biomedical optical measurement apparatus employing a time-sharing light irradiating and receiving means has been described with reference to FIG. 13. Such improvement can be applied not only to the biomedical optical measurement apparatus equipped with a time-sharing light irradiating and receiving means but also to the biomedical optical measurement apparatus equipped with both a lock-in amplifier and a time-sharing light irradiating and receiving means. Particularly, the employment of the lock-in amplifier and the time-sharing light irradiating and receiving means as described above ensures confident actions and improves reliability. Moreover, the employment of both can make it easier to receive the inspection light at the light source and light-receiving units placed closely, thereby improves resolution regarding optical measurement.

INDUSTRIAL APPLICABILITY

According to the biomedical optical measurement apparatus of this invention, by storing digitized data of multiple reference signals in a storing means, the provision of the reference signal generating circuits of a number equal to that of frequencies of signals to be detected can be unnecessary, and the number of units required in the configuration of the lock-in amplifier can be reduced. Moreover, according to the biomedical optical measurement apparatus of this invention, changes in frequency can be easily coped with by only re-writing the data of the storing means and storing digitized reference signals with new frequencies. Moreover, according to the biomedical optical measurement apparatus of this invention, signals can be detected without deteriorating S/N ratio even when there is phase difference between the signals to be detected and reference signals.

The invention claimed is:

1. A biomedical optical measurement apparatus comprising:
   a light source means for generating an inspection light containing multiple lights modulated at a given number of different frequencies,
   a light-receiving means for receiving the light generated at said light source means and passed through an object to be examined and for outputting synthesized signals made of a given number of electric signals each having a different frequency and an intensity corresponding to the received light, and
   a detection means for detecting a signal with the same frequency as a frequency of a reference signal having a frequency corresponding to frequencies of modulated multiple lights in the synthesized signals, wherein
   said detection means comprises:
   an analog-digital conversion means for outputting digitized synthesized signal data by converting said synthesized signals having different frequencies to a digital signal,
   a storage means for storing digitized data of a number of reference signals, where the number of reference signals is equal to the number of the synthesized signals output from the light-receiving means,
   a delaying means for delaying said reference signals data read out from the storage means based on phase differences between said synthesized signals data output from said analog-digital conversion means and said reference signals data read out from the storage means,
   a digital multiplication means for multiplying said synthesized signals data output from said analog-digital conversion means by said reference signals data delayed by the delaying means and for outputting the product of multiplication, and
   a digital band-limitation means for taking out DC data from the output from said digital multiplication means.

2. The biomedical optical measurement apparatus of claim 1, wherein said digital multiplication means and said digital band limitation means are composed by a digital signal processor.

3. The biomedical optical measurement apparatus of claim 1, further comprising a function generating means for inputting the digitized data of said reference signals and for generating a function that becomes "0" or "close to 0" near a level changing point of the digitized data.

4. The biomedical optical measurement apparatus of claim 1, wherein a digital signal processor including said digital multiplying means and said digital band-limitation means is provided for each modulation frequency.

5. The biomedical optical measurement apparatus of claim 4, wherein the digital multiplying means further comprises:
   a first digital multiplication means for multiplying digitized data of input signals outputted from said analog-digital conversion means by the digitized data of the reference signals read out from said storage means and for outputting the product of multiplication, and
   a second digital multiplication means for multiplying the output from said first digital multiplication means by a low-pass filter coefficient and for outputting the product of multiplication.

6. The biomedical optical measurement apparatus of claim 1, wherein said digital band-limitation means has an attenuation-band frequency fa satisfying fp≧2fa when a frequency interval (pitch) of signals to be detected is fp.

7. The biomedical optical measurement apparatus of claim 1, further comprising a control means for controlling said light source means, said light-receiving means and said detection means, wherein said control means generates timing signals with a predetermined interval and controls irradiation of the inspection light from the light source means and signal detection by the detection means in a time-sharing manner according to the timing signal.

8. The biomedical optical measurement apparatus of claim 1, further comprising an amplifier for outputting multiple signals sequentially outputted from said light-receiving means as a continuous signal, and a control means for controlling the detection means, wherein a sampling time at the analog-digital conversion means is controlled by a timing signal outputted from said control means.

9. The biomedical optical measurement apparatus of claim 1, wherein the detection means further comprises:
   a clock means for generating timing signals for said analog-digital conversion means to perform analog-digital conversion at a specified sampling timing,
   a function generating means for generating a function which becomes "0" or "close to 0" near the sampling time of said input signals, and
   a digital multiplying means for multiplying the digitized data output from said analog-digital conversion means by the function from said function generating means, and outputting the product of the multiplication.

10. The biomedical optical measurement apparatus of claim 9, further comprising an integrating means for adding the output from said digital multiplying means posterior the digital multiplying means.

11. A biomedical optical measurement apparatus comprising:
   a light source means for generating multiple inspection lights modulated at different frequencies in a time-sharing manner,
   a light-receiving means for sequentially receiving the inspection light generated at said light source means and passed through an object to be examined and for outputting synthesized signals made of electric signals having different frequencies with an intensity corresponding to the received inspection light, and
   a detection means for detecting signals with the same frequency corresponding to frequencies of modulated multiple lights in the synthesized signals; wherein
   said detection means further comprises:
   an analog-digital conversion means for outputting digitized synthesized signals data by converting said synthesized signals having different frequencies to a digital signal,
   a clock means for generating a timing signal so that said analog-digital converting means can begin analog-digital conversion at a specified sampling timing,
   a function generating means for generating functions which become "0" or "close to 0" near the sampling time of said synthesized signals,
   a delaying means for delaying said functions based on phase differences between said synthesized signals data output from said analog-digital conversion means and said timing signal of said clock means, and
   a digital multiplying means for multiplying digitized synthesized signals outputted from said analog-digital converting means by the function of said function generating means and for outputting the product of multiplication.

12. The biomedical optical measurement apparatus of claim 11, further comprising an integrating means for adding the output from said digital multiplication means posterior the digital multiplication means.

13. A detection circuit for a biomedical optical measurement apparatus comprising;
   an analog-digital converting means for performing analog-digital conversion of input signals and for outputting digitized data of the input signal,
   a function generator for generating one or more functions to be selected from trigonometric function, Gaussian function, Hamming and Hanning window functions,
   a delaying means for delaying said functions based on phase differences between said digitized data output from said analog-digital conversion means and said functions generated from said function generator, and
   a multiplying means for multiplying output from said analog-digital converting means by the function generated from said function generator.

14. The detection circuit of claim 13, further comprising, posterior said multiplying means, adding means for feeding back the sum (results of addition) from itself and adding to the output from said multiplying means.

* * * * *